US008356593B2

(12) United States Patent
Cortez, Jr. et al.

(10) Patent No.: US 8,356,593 B2
(45) Date of Patent: Jan. 22, 2013

(54) DELIVERY TUBE FOR BREATHING GAS HEATING AND HUMIDIFICATION SYSTEM

(75) Inventors: Felino V. Cortez, Jr., Bowie, MD (US); Owen S. Bamford, Linthicum, MD (US); William F. Niland, Arnold, MD (US); George McGarrity, Centreville, MD (US); Peter Boyd, Charlottesville, VA (US)

(73) Assignee: Vapotherm, Inc., Stevensville, MD (US)

( * ) Notice: Subject to any disclaimer, the term of this patent is extended or adjusted under 35 U.S.C. 154(b) by 1215 days.

(21) Appl. No.: 12/175,899

(22) Filed: Jul. 18, 2008

(65) Prior Publication Data

US 2009/0056715 A1  Mar. 5, 2009

Related U.S. Application Data

(60) Provisional application No. 60/961,020, filed on Jul. 18, 2007, provisional application No. 60/981,270, filed on Oct. 19, 2007.

(51) Int. Cl.
*F23D 11/00* (2006.01)

(52) U.S. Cl. .................................. 128/203.26

(58) Field of Classification Search ............. 128/203.26, 128/200.24, 200.27, 201.13, 204.17, 911
See application file for complete search history.

(56) References Cited

U.S. PATENT DOCUMENTS

| 3,659,604 A | 5/1972 | Melville et al. |
| 3,903,216 A | 9/1975 | Allan |
| 4,010,748 A | 3/1977 | Dobritz |
| 4,036,919 A | 7/1977 | Komendowski et al. |
| 4,163,371 A | 8/1979 | Groninger |
| 4,319,566 A | 3/1982 | Hayward |
| 4,463,755 A | 8/1984 | Suzuki |
| 4,532,088 A | 7/1985 | Miller |
| 4,632,677 A | 12/1986 | Blackmer |
| 4,652,408 A | 3/1987 | Montgomery |
| 4,657,713 A | 4/1987 | Miller |
| 4,753,758 A | 6/1988 | Miller |
| 4,921,642 A | 5/1990 | LaTorraca |
| 4,955,372 A | 9/1990 | Blackmer |
| 5,031,612 A * | 7/1991 | Clementi ................. 128/204.14 |
| 5,036,847 A | 8/1991 | Boussignac et al. |
| 5,065,756 A | 11/1991 | Rapoport |

(Continued)

FOREIGN PATENT DOCUMENTS

WO  WO 2006/026387  3/2006

OTHER PUBLICATIONS

International Search Report for International Application No. PCT/US2008/008792 mailed on Dec. 18, 2008.

(Continued)

*Primary Examiner* — Loan Thanh
*Assistant Examiner* — Shila Jalalzadeh Abyane
(74) *Attorney, Agent, or Firm* — RatnerPrestia

(57) ABSTRACT

A delivery tube assembly for delivering a breathing gas to a patient, the delivery tube includes a first lumen having an upstream portion and a downstream portion. The lumen is configured to deliver the breathing gas from the upstream portion to the downstream portion. A second lumen is configured to flow an insulating gas around the first lumen. A method of insulating a breathing gas with an insulating gas and discharging the insulating gas to atmosphere is also disclosed.

14 Claims, 22 Drawing Sheets

U.S. PATENT DOCUMENTS

| | | | |
|---|---|---|---|
| 5,255,674 A | 10/1993 | Oftedal | |
| 5,349,946 A | 9/1994 | McComb | |
| 5,367,604 A | 11/1994 | Murray | |
| 5,445,143 A | 8/1995 | Sims | |
| 5,474,062 A | 12/1995 | DeVires | |
| 5,525,268 A | 6/1996 | Reens | |
| 5,558,084 A | 9/1996 | Daniell et al. | |
| 5,588,423 A | 12/1996 | Smith | |
| 5,623,922 A | 4/1997 | Smith | |
| 5,823,184 A | 10/1998 | Gross | |
| 5,901,705 A | 5/1999 | Leagre | |
| 6,010,118 A | 1/2000 | Milewicz | |
| 6,050,260 A | 4/2000 | Daniell | |
| 6,095,505 A | 8/2000 | Miller | |
| 6,102,037 A | 8/2000 | Koch | |
| 6,125,847 A | 10/2000 | Lin | |
| 6,129,082 A | 10/2000 | Leagre | |
| 6,152,132 A | 11/2000 | Psaros | |
| 6,244,576 B1 | 6/2001 | Tsai | |
| 6,256,454 B1 | 7/2001 | Dykes | |
| 6,349,724 B1 | 2/2002 | Burton | |
| 6,397,841 B1 | 6/2002 | Kenyon | |
| 6,410,465 B1 | 6/2002 | Lim | |
| 6,454,997 B1 * | 9/2002 | Divino et al. | 422/44 |
| 6,536,428 B1 | 3/2003 | Smith | |
| 6,550,476 B1 * | 4/2003 | Ryder | 128/201.13 |
| 6,554,260 B1 | 4/2003 | Lipscombe | |
| 6,718,974 B1 | 4/2004 | Moberg | |
| 6,824,127 B2 | 11/2004 | Park | |
| 6,918,389 B2 | 7/2005 | Seakins | |
| 6,938,619 B1 | 9/2005 | Hickle | |
| 6,997,183 B2 | 2/2006 | Koch | |
| 7,073,500 B2 | 7/2006 | Kates | |
| 7,077,135 B2 * | 7/2006 | Pagan | 128/205.23 |
| 7,080,645 B2 | 7/2006 | Genger et al. | |
| 7,081,560 B1 | 7/2006 | Lim | |
| 7,086,399 B2 | 8/2006 | Makinson | |
| 7,106,955 B2 | 9/2006 | Thudor | |
| 7,111,624 B2 | 9/2006 | Thudor et al. | |
| 7,137,388 B2 | 11/2006 | Virr | |
| 7,140,367 B2 | 11/2006 | White | |
| 7,146,979 B2 | 12/2006 | Seakins | |
| 7,250,035 B1 | 7/2007 | Ott | |
| 2001/0050080 A1 | 12/2001 | Seakins | |
| 2001/0054422 A1 | 12/2001 | Smith | |
| 2002/0195104 A1 | 12/2002 | Fini | |
| 2003/0236015 A1 | 12/2003 | Edirisuriya et al. | |
| 2004/0016432 A1 | 1/2004 | Genger et al. | |
| 2005/0022828 A1 * | 2/2005 | Fukunaga et al. | 128/911 |
| 2005/0178383 A1 | 8/2005 | Mackie | |
| 2006/0021615 A1 | 2/2006 | Kertzman | |
| 2006/0037613 A1 | 2/2006 | Kwok | |
| 2006/0113690 A1 | 6/2006 | Huddart | |
| 2006/0118111 A1 | 6/2006 | Pelerossi | |
| 2006/0130836 A1 | 6/2006 | Wixey et al. | |
| 2006/0184096 A1 | 8/2006 | Ott et al. | |
| 2006/0191531 A1 | 8/2006 | Mayer | |
| 2006/0213515 A1 | 9/2006 | Bremner | |
| 2006/0219243 A1 | 10/2006 | Walstrom | |
| 2006/0272639 A1 | 12/2006 | Makinson | |
| 2007/0175473 A1 | 8/2007 | Lewis et al. | |

OTHER PUBLICATIONS

Written Opinion of the International Searching Authority for International Application No. PCT/US2008/008792 mailed on Dec. 18, 2008.

U.S. Appl. No. 12/175,888 of Felino V. Cortez et al. filed Jul. 18, 2008.

U.S. Appl. No. 12/175,853 of Felino V. Cortez et al. filed Jul. 18, 2008.

U.S. Appl. No. 12/175,861 of Felino V. Cortez et al. filed Jul. 18, 2008.

* cited by examiner

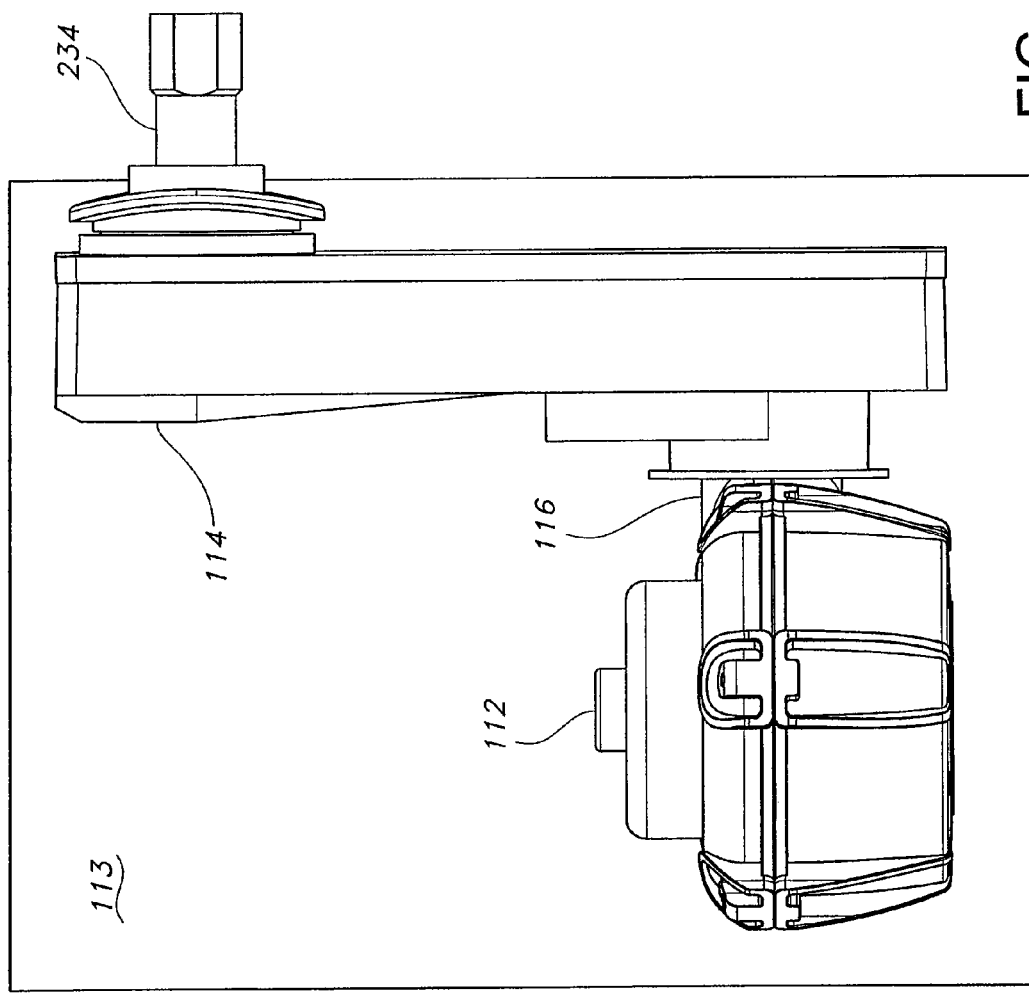

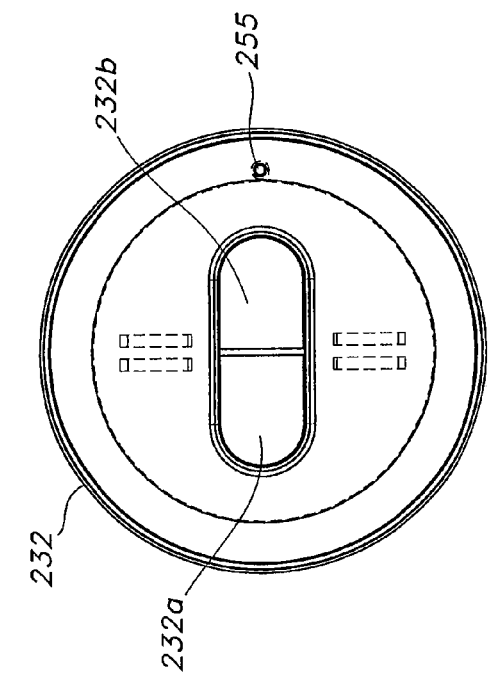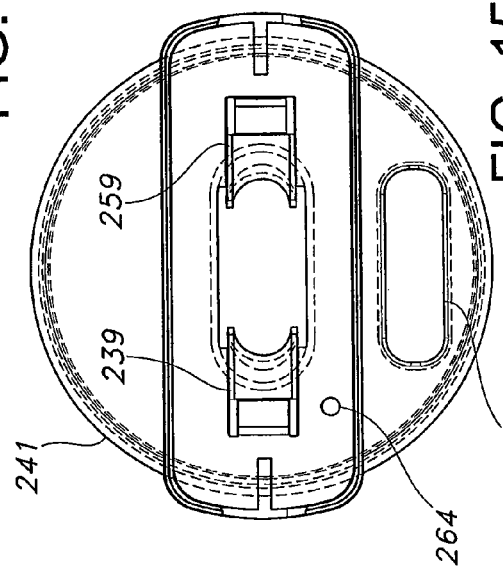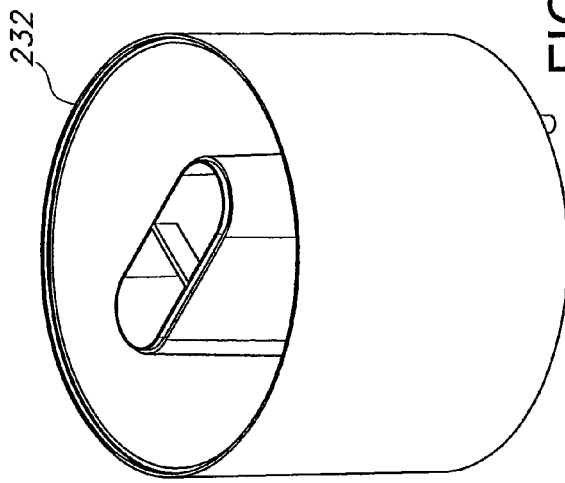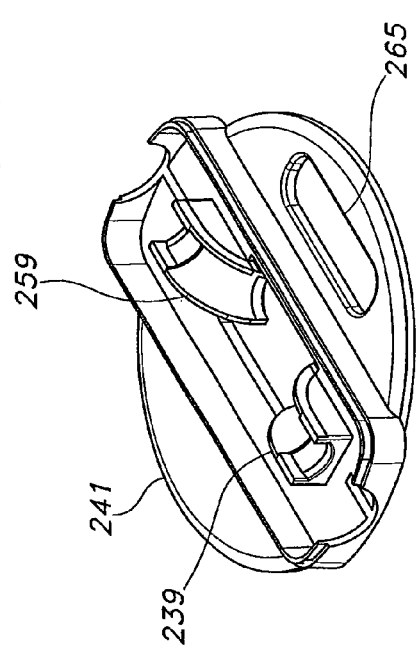

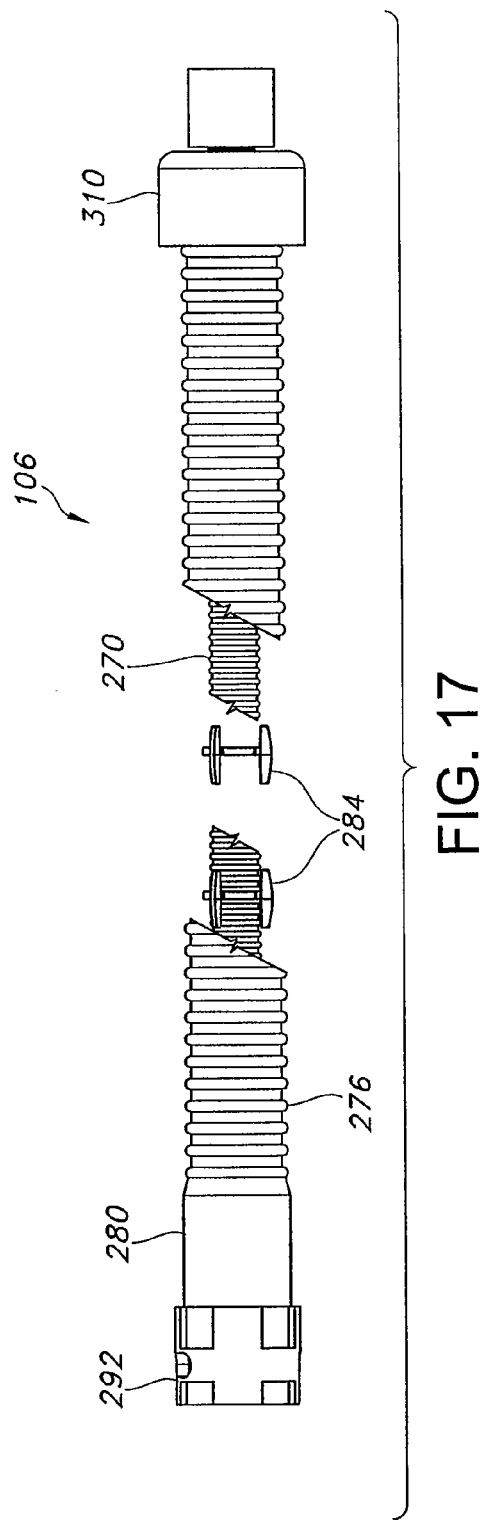
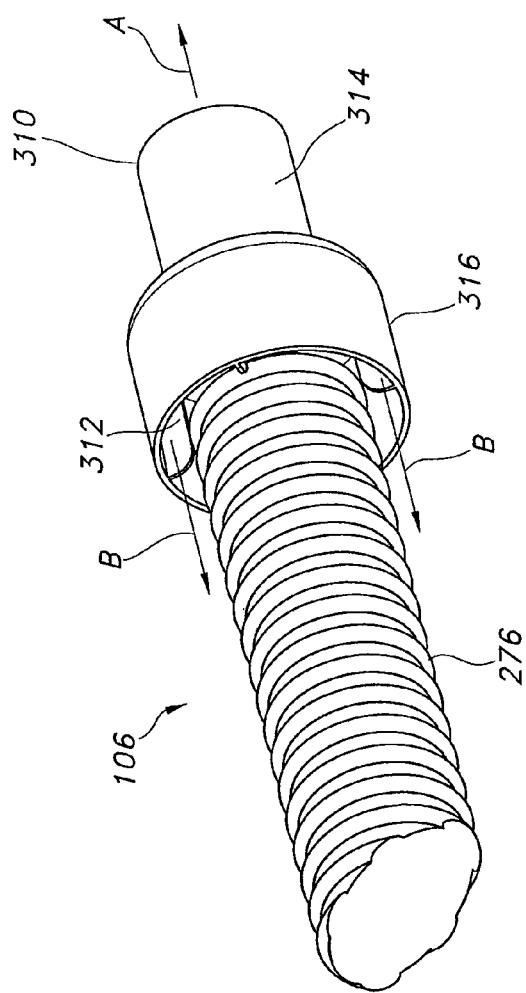

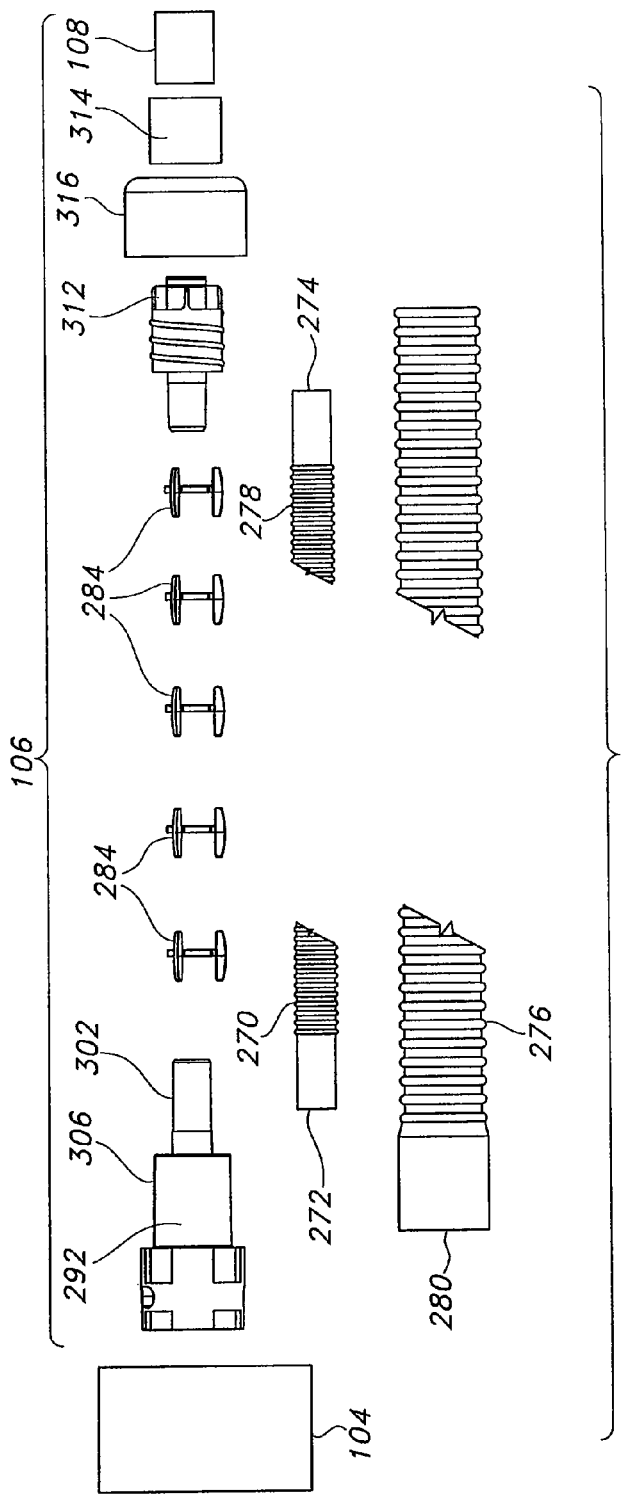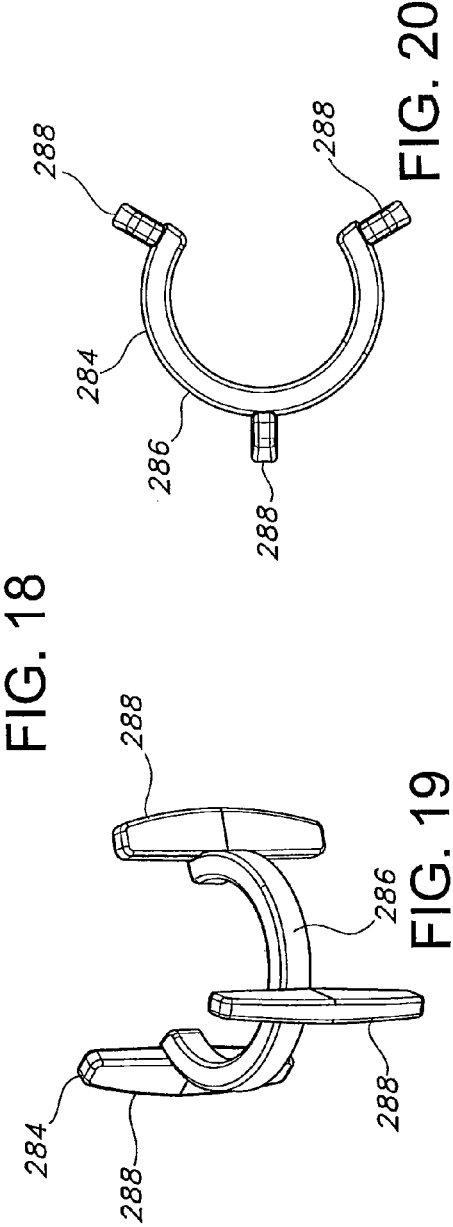

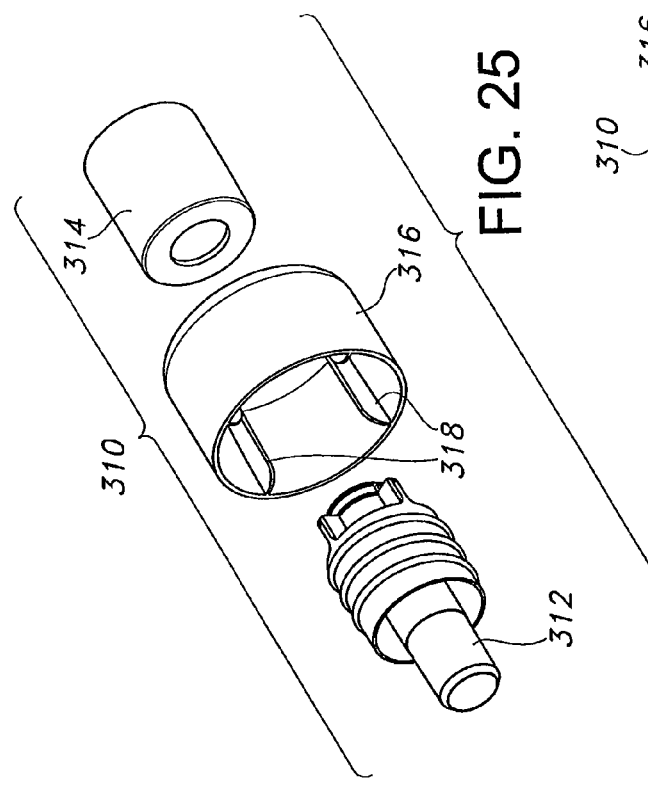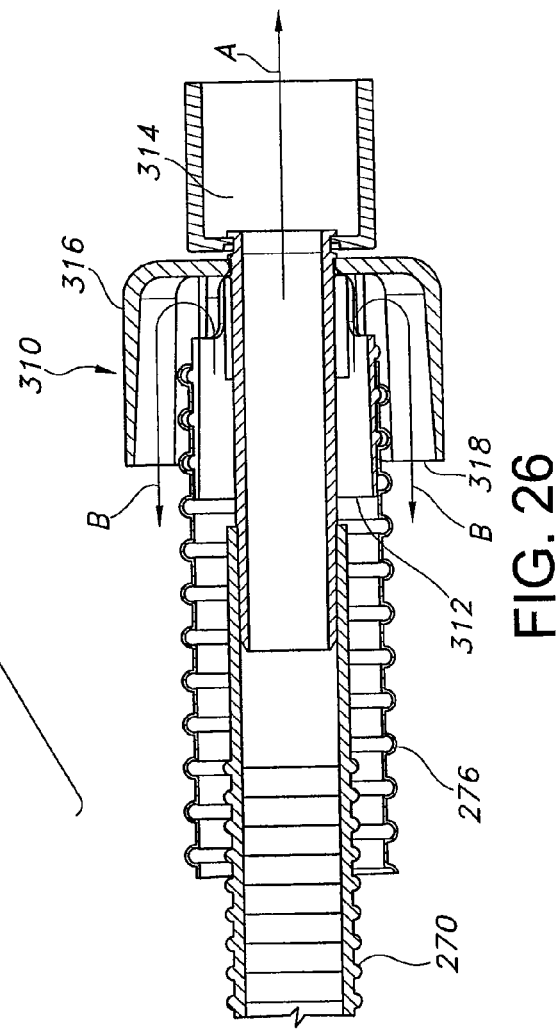

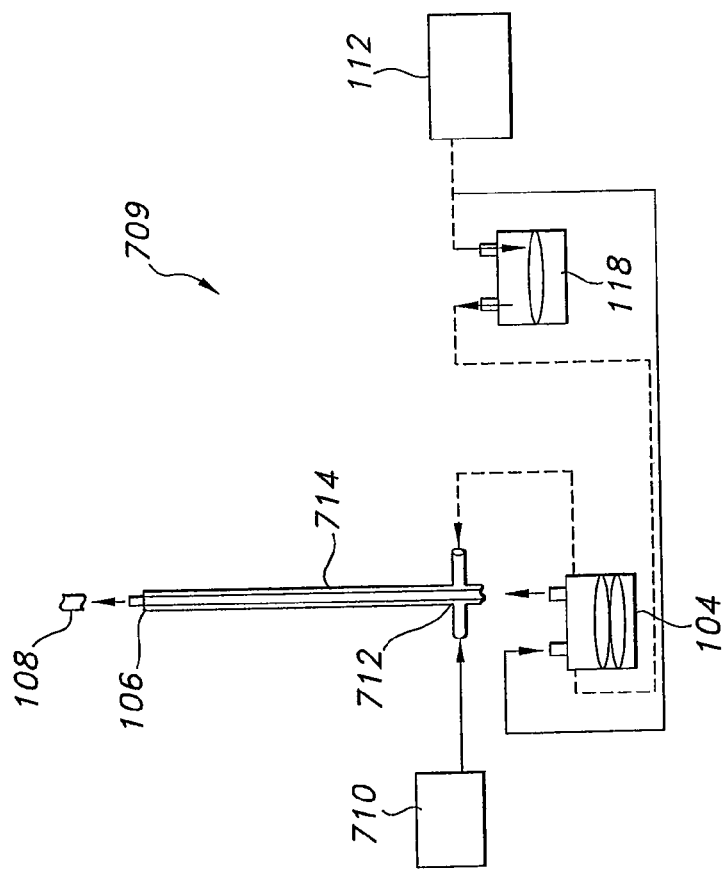
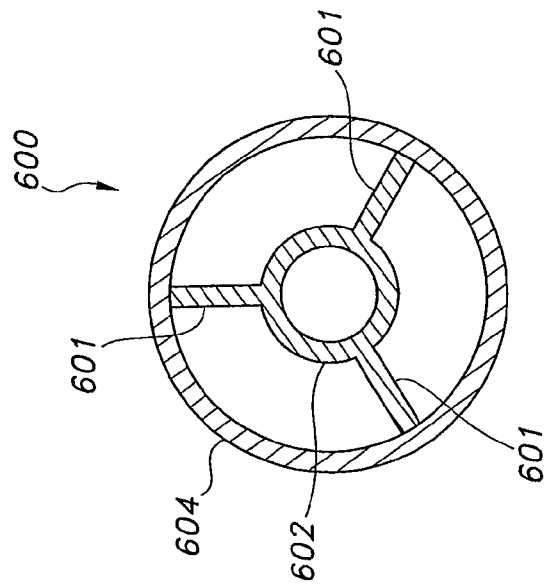
FIG. 29
FIG. 30

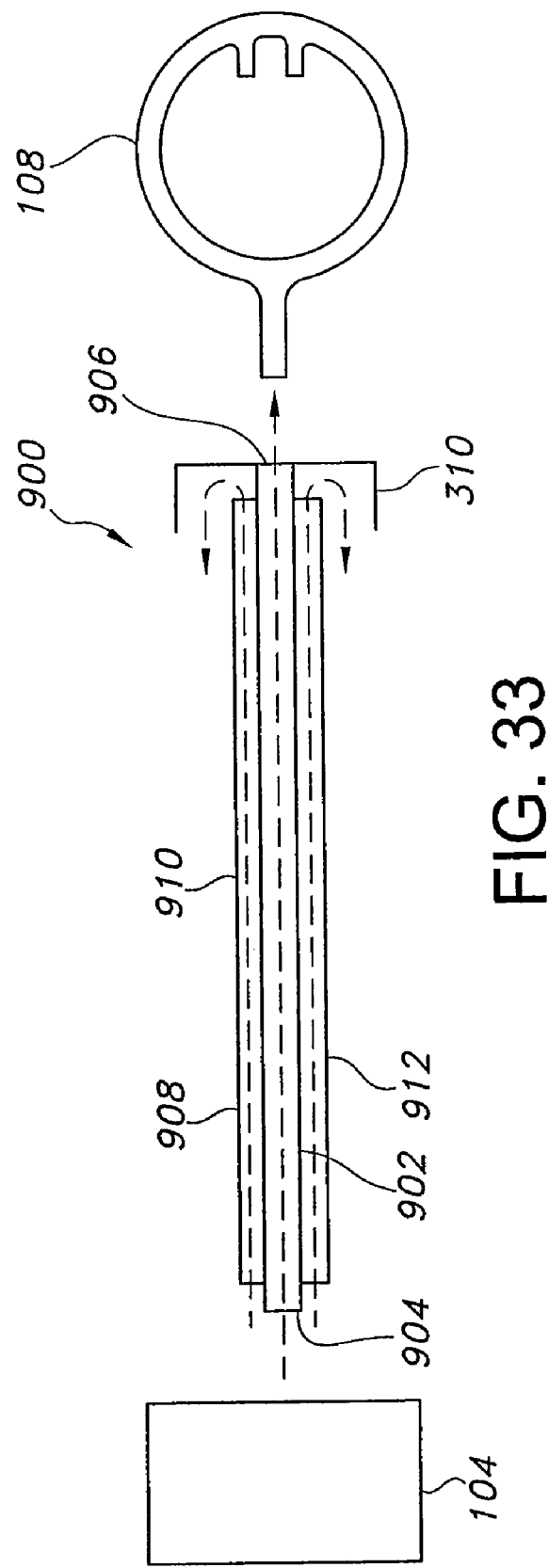

DELIVERY TUBE FOR BREATHING GAS HEATING AND HUMIDIFICATION SYSTEM

CROSS-REFERENCE TO RELATED APPLICATIONS

This application claims priority from U.S. Provisional Patent Application Ser. No. 60/961,020, filed on Jul. 18, 2007, which is incorporated by reference in its entirety, and U.S. Provisional Patent Application Ser. No. 60/981,270, filed on Oct. 19, 2007, which is incorporated by reference in its entirety. This application is related to copending application Ser. Nos. 12/175,861, 12/175,855, and 12/175,888, filed on even date herewith and incorporated by reference in their entireties.

FIELD OF THE INVENTION

This invention relates to respiratory tract therapy. More particularly, this invention relates to methods and apparatus that heat and humidify a breathing gas for delivery to the respiratory tract of a patient.

BACKGROUND OF THE INVENTION

Conventional methods of delivering gas (e.g., air, oxygen, oxygen-enriched air, and other breathing gas mixtures) to the respiratory tract of a patient often result in discomfort to the patient, especially when the gases are delivered over an extended period of time. A need remains for improved methods and apparatus for delivering breathing gas.

BRIEF SUMMARY OF THE INVENTION

Briefly, the present invention provides an apparatus for providing breathing gas to a patient. The apparatus includes a base unit configured to provide a first flow of gas and a second flow of gas and a humidification canister configured to be coupled to the base unit. The humidification canister includes a first gas flow path configured to receive and humidify the first flow of gas. A delivery tube assembly is configured to be coupled to the humidification canister. The delivery tube assembly includes a first lumen configured for fluid communication with the first gas flow path to receive the humidified first flow of gas and a second lumen configured to receive the second flow of gas.

The present invention also provides a heated and humidified breathing gas apparatus including a source of gas and a humidification chamber operatively coupled to the source of gas. The humidification chamber is configured to heat and humidify a first portion of the gas generated by the source of gas. An insulation chamber is operatively coupled to the source of gas and at least partially surrounds the humidification chamber. A multilumen delivery tube assembly has a first lumen in fluid communication with the humidification chamber and a second lumen adjacent the first lumen in fluid communication with the insulation chamber.

Further, the present invention provides a method for providing breathing gas to a patient that includes generating a first flow of gas and a second flow of gas; passing the first flow of gas along a first gas flow path and the second flow of gas along a second gas flow path, humidifying the first flow of gas in the first gas flow path, insulating at least a portion of the first flow of gas passing along the first gas flow path with the second flow of gas passing along the second gas flow path, and delivering the humidified first flow of gas to the patient for inhalation by the patient.

Additionally, the present invention provides a method of delivering heated and humidified breathing gas to a patient. The method includes generating a gas flow, dividing the gas flow into a breathing gas flow and an insulating gas flow, heating and humidifying the breathing gas flow, and delivering the heated and humidified breathing gas flow to the patient.

Further, the present invention provides a base unit for use in a breathing gas heating and humidification apparatus. The base unit includes a gas source configured to generate an initial gas flow. The gas source has a gas source outlet. A flow divider is in fluid communication with the gas source outlet. The flow divider is configured to divide the initial gas flow into a first flow of gas and a second flow of gas. The flow divider includes a first compartment including a first gas flow path for the first flow of gas and a second compartment including a second gas flow path for the second flow of gas. A heater is disposed in the second compartment.

Also, the present invention provides a base unit for use in a breathing gas heating and humidification apparatus. The base unit includes a blower configured to generate a gas flow and a flow divider in fluid communication with the blower. The divider is configured to divide the gas flow into a first portion of the gas flow and a second portion of the gas flow.

The present invention further provides a method for use in generating breathing gas and insulating gas from a gas source. The method includes generating a flow of gas, dividing the flow of gas into a first flow of gas and a second flow of gas, and passing the first flow of gas for delivery to a patient for inhalation.

Additionally, the present invention provides a humidification canister for humidifying a breathing gas. The humidification canister includes a fluid supply configured to supply a fluid. A first gas flow path is in fluid communication with the fluid supply. The first gas flow path is configured to humidify the breathing gas with the fluid. A second gas flow path at least partially surrounds the first gas flow path.

The present invention further provides a method of pressurizing a supply of humidification fluid within a humidification that includes generating a flow of a breathing gas along a first gas flow path, generating a flow of an insulating gas along a second gas flow path, providing a supply of a humidification fluid within the humidification canister to humidify the breathing gas, and providing fluid communication between the second gas flow path and the supply of the humidification fluid to pressurize the supply of the humidification fluid with the insulating gas.

The present invention also provides a method of insulating a breathing gas in a humidification canister using a gas. The method includes directing a flow of a breathing gas along a first gas flow path including the humidification chamber and directing a flow of an insulating gas along a second gas flow path including an insulating chamber at least partially surrounding the humidification chamber where the insulating gas at least partially insulates the breathing gas.

Additionally, the present invention provides a humidification canister for humidifying a flow of breathing gas. The humidification canister includes means for supplying a fluid, means for humidifying a first gas flow with the fluid along a first gas flow path, and means for at least partially insulating the first gas flow with a second gas flow.

Further, the present invention provides a delivery tube assembly for delivering a breathing gas to a patient. The delivery tube includes a first lumen having an upstream portion and a downstream portion. The lumen is configured to deliver the breathing gas from the upstream portion to the downstream portion. A second lumen is configured to flow an insulating gas around the first lumen.

The present invention also provides a delivery tube assembly configured to be coupled to a humidifier. The delivery tube assembly comprises an inner lumen with an upstream portion configured to receive humidified breathing gas from the humidifier and a downstream portion configured to deliver the humidified breathing gas to a breathing device and an outer lumen surrounding the inner lumen that is configured for coupling to the humidifier to receive an insulating gas.

The present invention further provides a delivery tube assembly for delivering a breathing gas to a patient. The delivery tube includes an inner lumen adapted to transmit a breathing gas and an outer lumen at least partially surrounding the inner lumen. The outer lumen is adapted to transmit an insulating gas and discharge the insulating gas to atmosphere. A diverter assembly is positioned to divert the insulating gas being discharged from the outer lumen to the atmosphere.

Further, the present invention provides a method of insulating heated and humidified breathing gas with an insulating gas in a delivery tube assembly having a first lumen and a second lumen. The method includes flowing the heated and humidified breathing gas through the first lumen and flowing the insulating gas through the second lumen where the insulating gas at least partially insulates the heated and humidified breathing gas.

Also, the present invention provides a method of insulating a breathing gas with an insulating gas and discharging the insulating gas to atmosphere. The method includes receiving the breathing gas in an upstream end of a delivery tube; receiving the insulating gas in the upstream end of the delivery tube; discharging the breathing gas from a downstream end of the delivery tube into a breathing device; flowing the insulating gas from the upstream end of the delivery tube, through the delivery tube, to the distal end of the delivery tube; and discharging the insulating gas from the delivery tube to atmosphere.

BRIEF DESCRIPTION OF THE DRAWINGS

The foregoing summary, as well as the following detailed description of exemplary embodiments of the invention, will be better understood when read in conjunction with the appended drawings, which are incorporated herein and constitute part of this specification. For the purposes of illustrating the invention, there are shown in the drawings exemplary embodiments of the present invention. It should be understood, however, that the invention is not limited to the precise arrangements and instrumentalities shown. In the drawings, the same reference numerals are employed for designating the same elements throughout the several figures. In the drawings:

FIG. 3 is a side view of a blower and gas heater illustrated in FIG. 2;

FIG. 14 is a perspective view of a fluid supply reservoir used in the humidification canister illustrated in FIGS. 10 and 11;

FIG. 14A is a top plan view of the fluid supply reservoir illustrated in FIG. 14;

FIG. 15 is a perspective view of a lid bottom used in the humidification canister illustrated in FIGS. 10 and 11;

FIG. 15A is a top plan view of the lid bottom illustrated in FIG. 15;

FIG. 17 is a side view, partially broken away, of a delivery tube assembly used in the apparatus illustrated in FIG. 1;

FIG. 18 is an exploded side view of the delivery tube assembly illustrated in FIG. 17;

FIG. 19 is a perspective view of an exemplary spacer used in the delivery tube assembly illustrated in FIGS. 17 and 18;

FIG. 20 is a top plan view of the spacer illustrated in FIG. 19;

FIG. 24 is a perspective view of a downstream end of the delivery tube assembly illustrated in FIGS. 17 and 18;

FIG. 25 is an exploded perspective view of a diverter assembly used in the delivery tube assembly illustrated in FIGS. 17 and 18;

FIG. 26 is a side view, in section, of the diverter assembly illustrated in FIG. 24;

FIG. 29 is a schematic drawing of an apparatus for providing breathing gas to a user according to another exemplary embodiment of the present invention;

FIG. 30 is a sectional view of a delivery tube assembly according to another exemplary embodiment of the present invention;

FIG. 33 is a schematic view of an apparatus for providing breathing gas to a user according to another exemplary embodiment of the present invention.

DETAILED DESCRIPTION OF THE INVENTION

Figure 1:
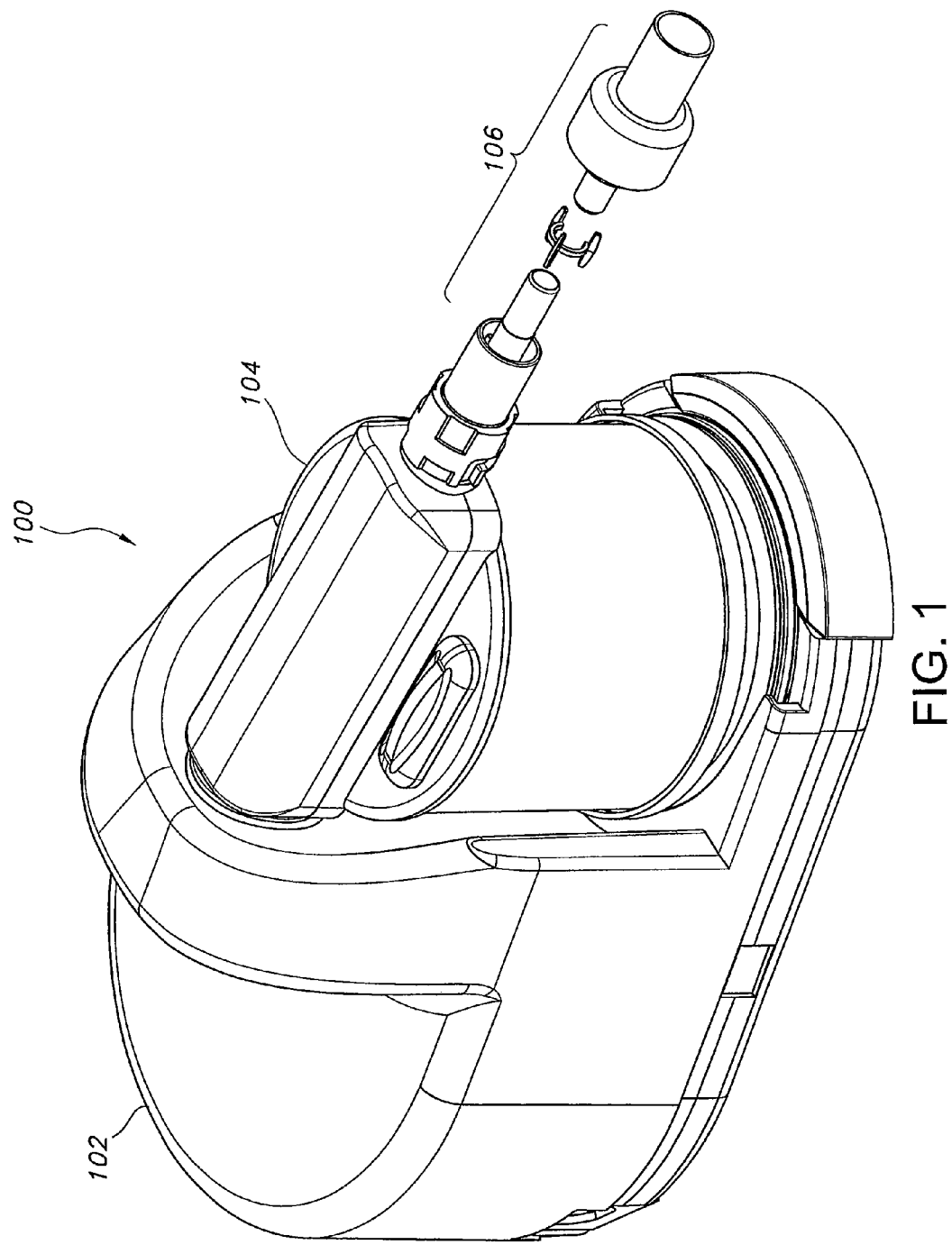
FIG. 1 is a perspective view of an apparatus for providing breathing gas to a user according to a first exemplary embodiment of the present invention.

Although the invention is illustrated and described herein with reference to specific embodiments, the invention is not intended to be limited to the details shown. Rather, various modifications may be made in the details within the scope and range of equivalents of the disclosure without departing from the invention. As used herein, the term "upstream" is defined to mean a direction farther from a user (i.e., a person receiving breathing gas) along a fluid flow path, and the term "downstream" is defined to mean a direction closer to the user along the fluid flow path. The terms "insulate," "insulating," and "insulation" are used herein to mean preventing or reducing temperature loss in fluid flowing along a fluid flow path, and/or, in certain circumstances, raising the temperature of the fluid flowing along the fluid flow path.

The invention is best understood from the following detailed description when read in connection with the accompanying drawing figures, which show exemplary embodiments of the invention selected for illustrative purposes. The invention will be illustrated with reference to the figures. Such figures are intended to be illustrative rather than limiting and are included herewith to facilitate the explanation of the present invention.

Referring generally to the figures, a breathing gas system according to an exemplary embodiment of the present invention is provided to heat, humidify and control patient respiratory gases. Warm, humidified gas is generated by the system and delivered to the user via a disposable and/or reusable humidification canister and an insulated delivery tube that is attached to a user interface, such as a nasal cannula.

In an exemplary embodiment, heat and humidification may be provided through an exchange medium that is part of the humidification canister. The exemplary medium forms a semi-permeable membrane between a water source (e.g., reservoir) and a humidification chamber within the humidification canister. This medium acts as the interface to transfer heat and molecular water vapor from the water source to the breathing gases by allowing heated molecules of water to transpire across the membrane into the breathing gases in the humidification chamber. The medium may also act as a valve, restricting the amount of water that is vaporized. Optionally, the medium may be omitted.

The delivery tube and humidification canister provide pathways for heated air generated with heat from an internal heater, for example, to surround or substantially surround the humidification chamber and gas delivery tube, thereby reducing heat loss (and/or providing heat gain) as the gas makes its way through the system to the user, via a cannula or a mask, for example. This arrangement minimizes water condensation and loss of beneficial heat and humidity before the breathing gas is delivered to the user's airway and allows the temperature of the breathing gas to be regulated independently from the addition of water vapor into the breathing gas.

In an exemplary embodiment, a system used to thermally insulate a breathing gas with insulating gas is disclosed. The insulating gas is provided by a source, heated to a specified temperature, and then provided to a breathing gas delivery tube. The delivery tube includes an inner lumen through which the breathing gas is delivered from a breathing gas source to the user, and an outer jacket through which the insulating gas travels such that the insulating gas insulates the breathing gas as both the insulating gas and the breathing gas travel through the delivery tube. After the insulating gas has insulated the breathing gas, the insulating gas may be exhausted to atmosphere. Alternatively, the insulating gas may be recirculated. Insulating gas is used to minimize heat loss of (and/or provide heat gain to) the breathing gas as the breathing gas travels from the humidification chamber to the user, thereby reducing rainout. Additionally, the use of the insulating gas allows adjustment to the temperature of the breathing gas without changing the water vapor content in the breathing gas, thereby adjusting relative humidity for added comfort.

Figure 2:
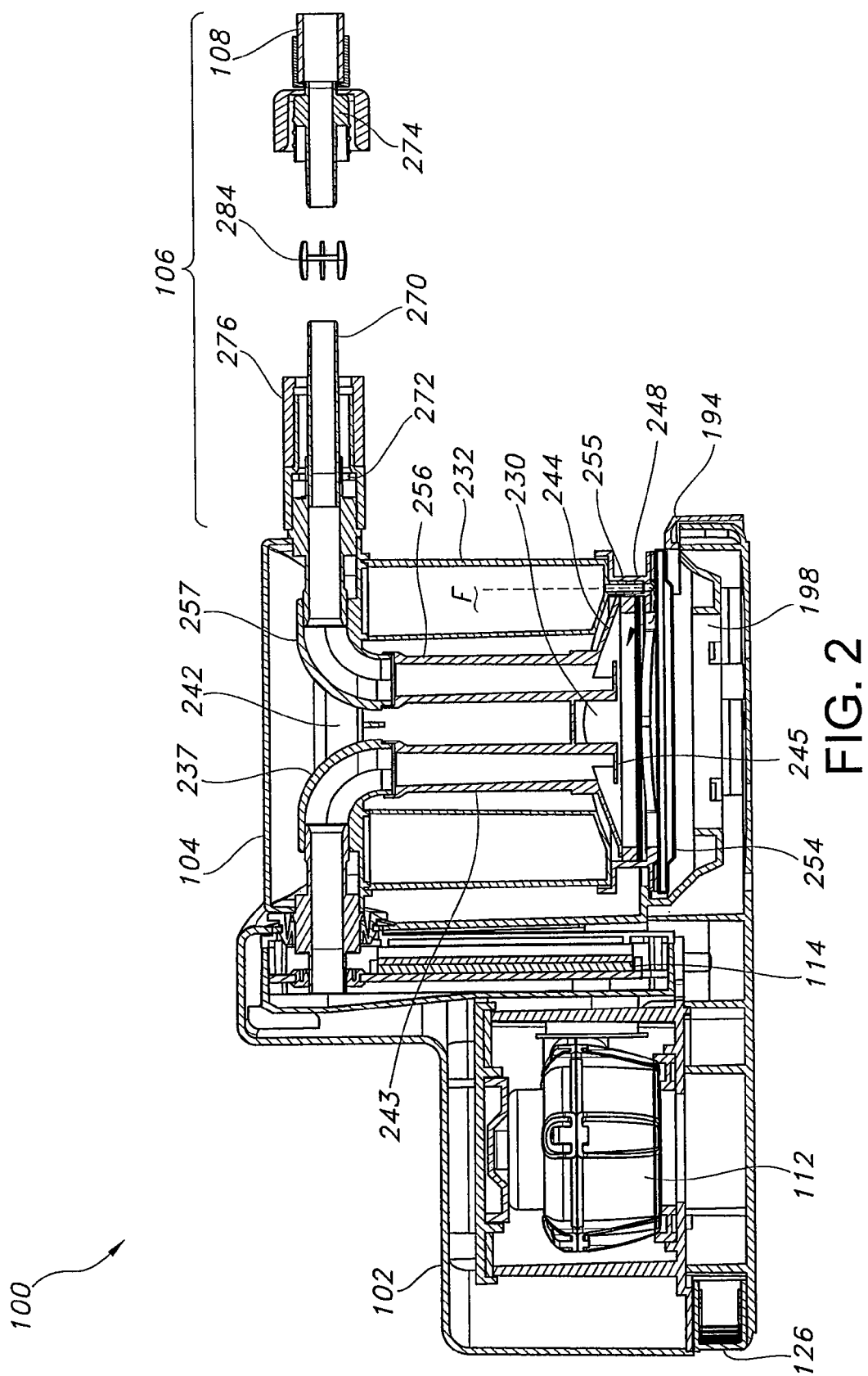
FIG. 2 is a side view, partially in section, of the breathing gas apparatus of FIG. 1.

Referring specifically to FIGS. 1 and 2, breathing gas system 100 includes a base unit 102 configured to generate a first flow, or portion, of gas and a second flow, or portion, of gas. A humidification canister 104 is configured to be coupled to base unit 102. Humidification canister 104 may be a reusable and/or disposable unit that is replaced after a specified period of time, such as after a prescribed number of days of use, a prescribed duration of use, or some other predetermined operating parameter.

A delivery tube assembly 106 is coupled to humidification canister 104 (preferably releasably coupled). Delivery tube assembly 106 may be a reusable and/or disposable unit that is replaced after a specified period, such as after a prescribed number of days of use, a prescribed duration of use, or some other predetermined operating parameter.

As shown if FIG. 2, a user device, such as, for example, a nasal cannula 108, is configured to be releasably coupled to delivery tube assembly 106. Exemplary nasal cannulae are disclosed in U.S. patent application Ser. Nos. 11/940,793 and 11/940,867, which are both owned by the Assignee of the present invention and are incorporated herein by reference in their entireties.

Figure 3A:
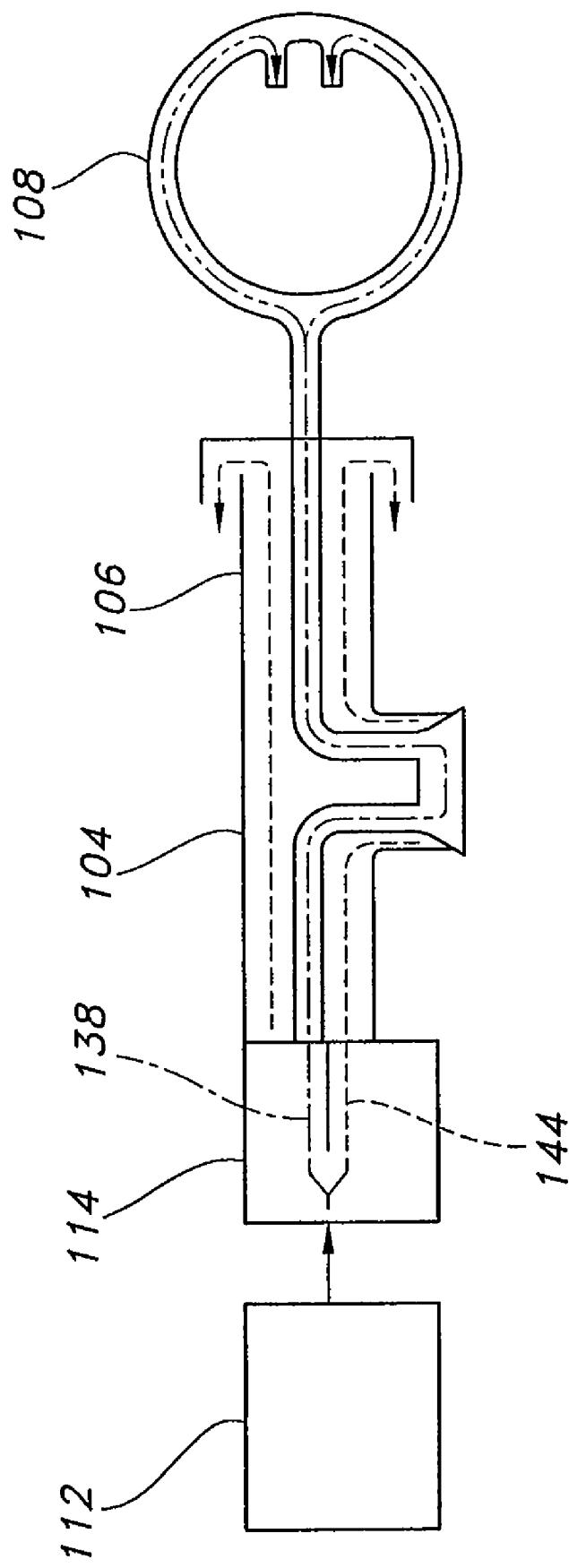
FIG. 3A is a schematic view of a first gas flow path and a second gas flow path through the breathing gas apparatus illustrated in FIG. 1.

Referring to FIGS. 2, 3 and 3A, base unit 102 includes a gas flow source 113 and a fluid heater 198 configured to heat a fluid in humidification canister 104. Illustrated base unit 102 includes a gas flow source 113, such as, for example, a blower 112 configured to deliver an initial flow of gas and a flow divider 114 in fluid communication with an outlet 116 of blower 112. As shown in FIG. 3A, flow divider 114 is configured to divide the initial flow of gas into a first flow of gas along a first gas flow path 138 (indicated by alternating dots and dashes) and a second flow of gas along a second gas flow path 144 (indicated by the dots).

Figure 28:
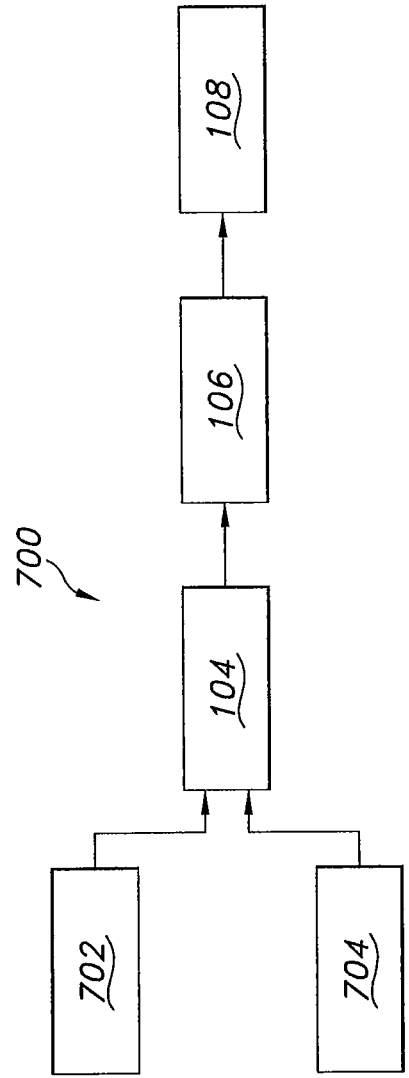
FIG. 28 is a schematic drawing of an apparatus for providing breathing gas to a user according to another exemplary embodiment of the present invention.

In an exemplary embodiment, blower 112 may be a single source. In another exemplary embodiment, as will be described with reference to FIG. 28, blower 112 may include a plurality of sources.

An exemplary blower 112 may be a model number 939_3020_007 manufactured by EBM Papst, Inc. of Farmington, Conn. Exemplary blower 112 may deliver air from outlet 116 of blower 112 at a delivery flow rate between about 1 liter per minute and about 150 liters per minute.

Blower 112 provides an initial flow rate, which is divided by flow divider 114 into a first flow of gas to be delivered to the user as a breathing gas at a desired delivery flow rate and a second flow of gas to be used as an insulating gas to insulate the breathing gas. While a desired delivery flow rate may be set, an actual flow rate of the first flow of gas being delivered to the user may be greater than the delivery flow rate during user inhalation and an actual flow rate of the first flow of gas being delivered to the user may be less than the delivery flow rate during user exhalation. Additionally, the initial flow rate may remain generally constant, with the actual flow rate of the second flow of gas decreasing as the flow rate of the first flow of gas increases (e.g., due to patient inhalation), and with the actual flow rate of the second flow of gas increasing as the flow rate of the first flow of gas decreases (e.g., due to patient exhalation).

Figure 4:
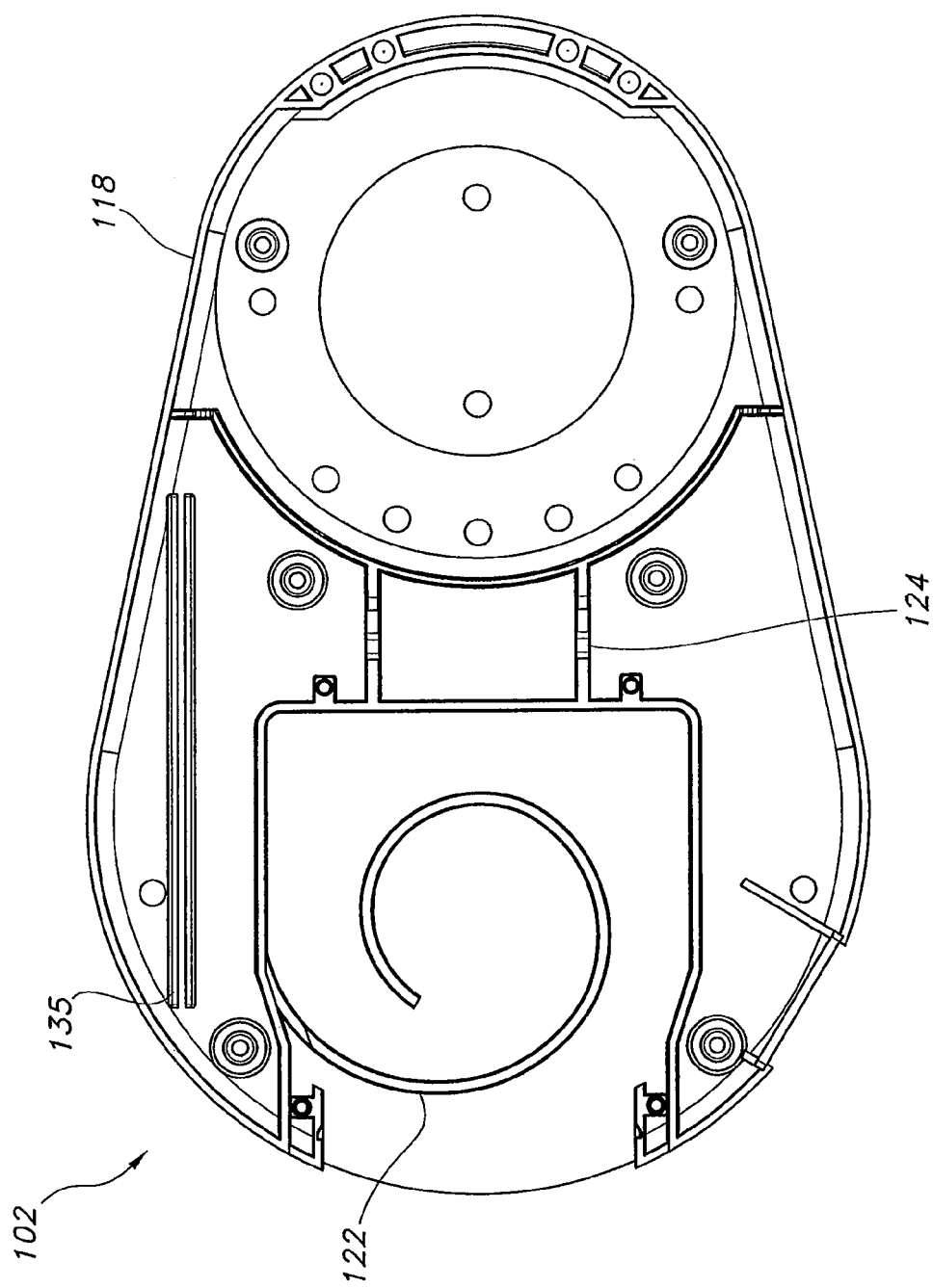
FIG. 4 is a top view of a bottom portion of the base unit of the apparatus illustrated in FIG. 1.
Figure 5:
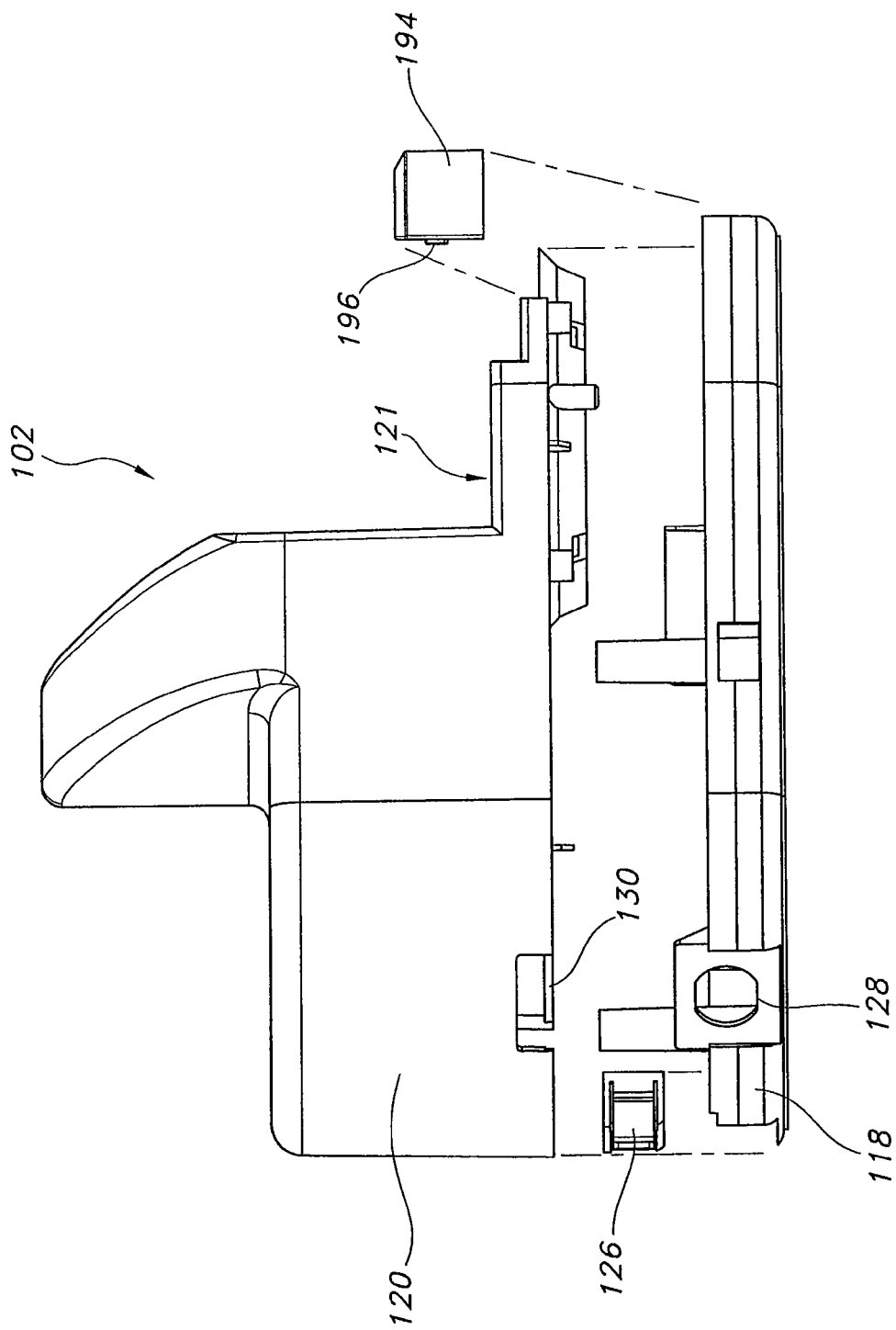
FIG. 5 is a side exploded view of elements of the base unit of the apparatus illustrated in FIG. 1.

Referring now to FIGS. 4 and 5, base unit 102 includes a case bottom 118 that receives and retains blower 112 (not shown in FIGS. 4 and 5) and other components. Base unit 102 also includes a case top 120 that fits over blower 112 and the components and attaches to case bottom 118. Case top 120 also includes a receptacle 121 for receiving and holding humidification canister 104 in contact with fluid heater 198. Blower 112 may be inserted into case bottom 118 and covered by case top 120.

Case bottom 118 includes a receptacle 122 for receiving and holding blower 112. Case bottom 118 also includes a receptacle 124 for receiving and holding flow divider 114 (not shown in FIGS. 4 and 5) such that flow divider 114 may be located between blower 112 and humidification canister 104 (not shown in FIGS. 4 and 5).

A filter cartridge 126 is releasably coupled to base unit 102. Filter cartridge 126 is used to filter air from atmosphere prior to entering blower 112. Filter cartridge 126 removes airborne particulates that may be harmful to the user if inhaled. Filter cartridge 126 may be snap fit to case bottom 118.

Case bottom 118 also includes a generally oval shaped opening 128 therein and case top 120 includes a generally rectangular mating opening 130 therein through which an electronic interface 132 (shown schematically if FIG. 9) extends. In an exemplary embodiment, interface 132 may be a USB port that allows an operator, such as a physician or a respiratory therapist, to couple system 100 to an external device, such as a computer (not shown), in order to program system 100 to meet the needs of the particular user or to extract operating data from system 100.

Interface 132 is electronically coupled to a printed circuit (PC) board 134 (shown schematically in FIG. 9) or other electronic controller that governs the operation of system 100. PC board 134 may be removably inserted into a PC board slot 135 in case bottom 118.

Referring to FIGS. 3, 3A, and 6-8, flow divider 114 comprises a first compartment 136 including first gas flow path 138 for the first flow of gas. First gas flow path 138 is configured to be coupled to humidification canister 104 for humidification of the first flow of gas. First compartment 136 also includes a first compartment discharge port 140.

Flow divider 114 further includes a second compartment 142 including second gas flow path 144 for the second flow of gas. Second gas flow path 144 is configured to receive the second flow of gas and to be coupled to humidification canister 104 to insulate at least a portion of first gas flow path 138. Second compartment 142 also includes a second compartment discharge port 146 in line with first compartment discharge port 140.

Illustrated flow divider 114 is constructed from a box 148 having an open face 150. A rear wall 152 of box 148 includes a circular opening 154 disposed proximate to the bottom of box 148. A rubber grommet 156 is disposed within circular opening 154. Grommet 156 is coupled to outlet 116 of blower 112 to receive gas generated by blower 112.

A cover 158 is disposed over open face 150 of box 148, forming a generally closed compartment. Cover 158 includes second compartment discharge port 146 disposed proximate to the top of cover 158. A rubber inlet grommet 161 is disposed within second compartment discharge port 146. Inlet grommet 161 is coupled to humidification canister 104 to discharge the gas flow generated by blower 112 from flow divider 114 to humidification canister 104.

A back-up plate 162 is disposed within box 148 to separate box 148 into first compartment 136 and second compartment 142. Back-up plate 162 includes first compartment discharge port 140 disposed proximate to the top of back-up plate 162, co-axially aligned with second compartment discharge port 146 in cover 158. A rubber back-up plate grommet 170 is disposed within first compartment discharge port 140 of back-up plate 162.

Figure 6:
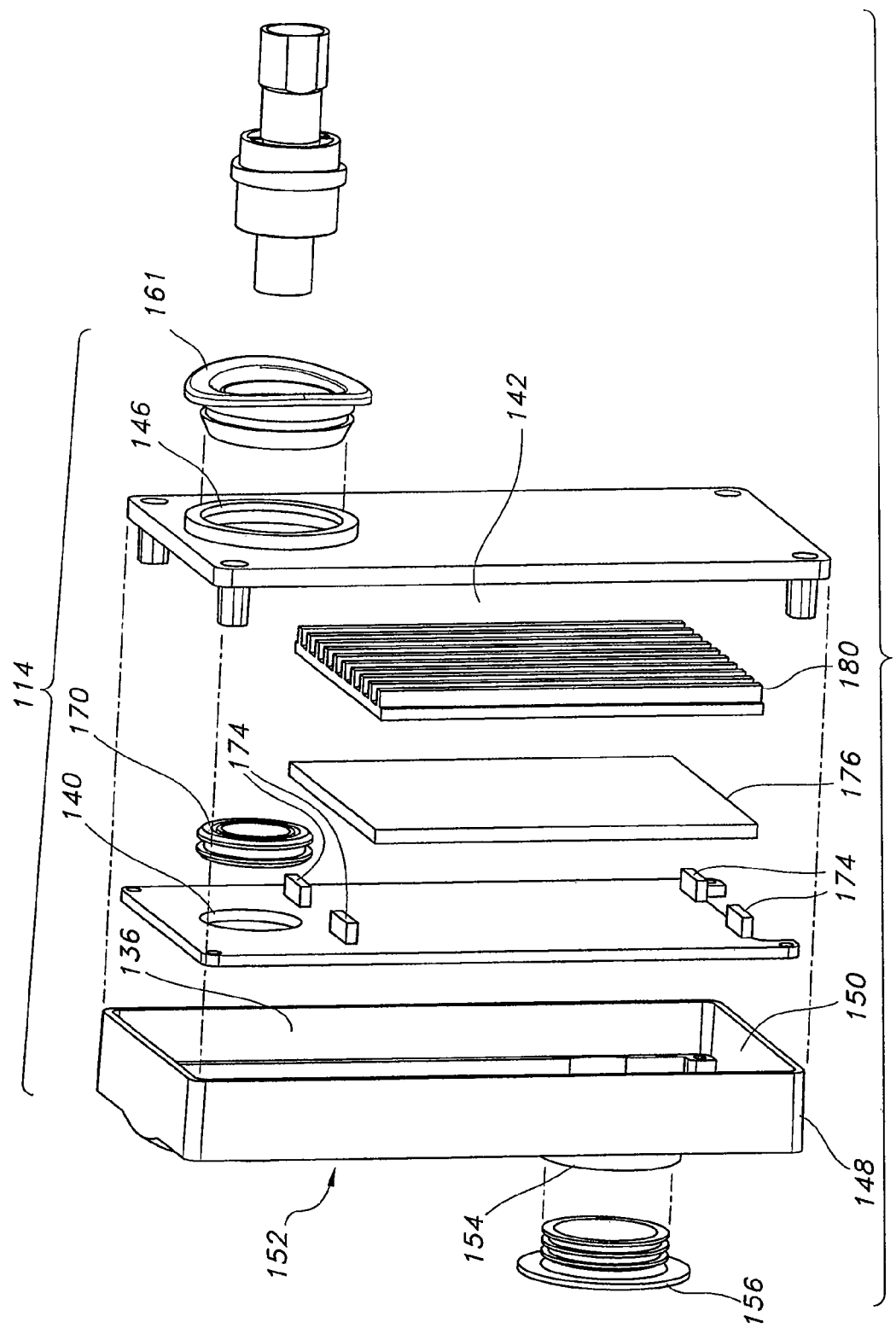
FIG. 6 is an exploded perspective view of a gas heater used in the apparatus illustrated in FIG. 1.
Figure 7:
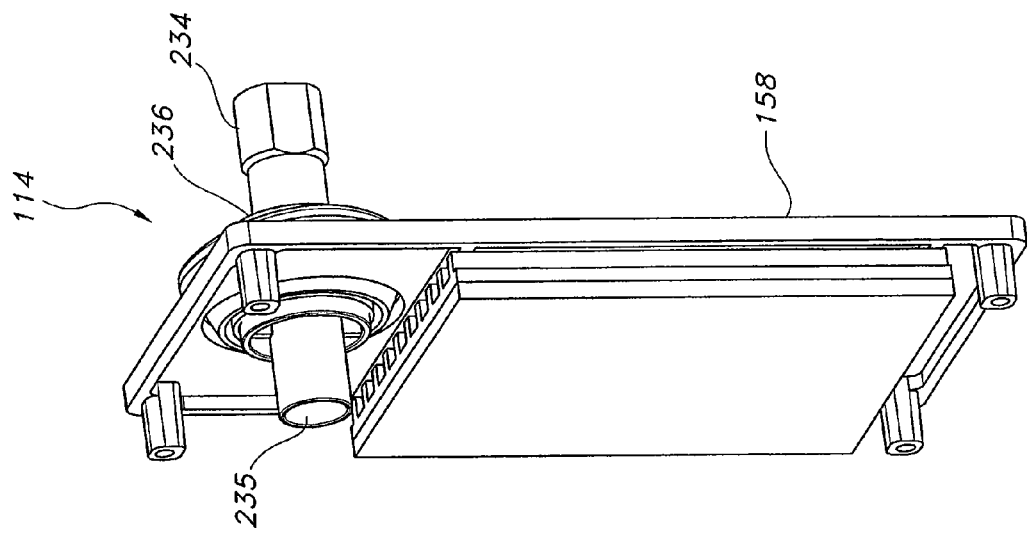
FIG. 7 is a perspective view of the gas heater illustrated in FIG. 6, with a box portion of the gas heater removed.
Figure 8:
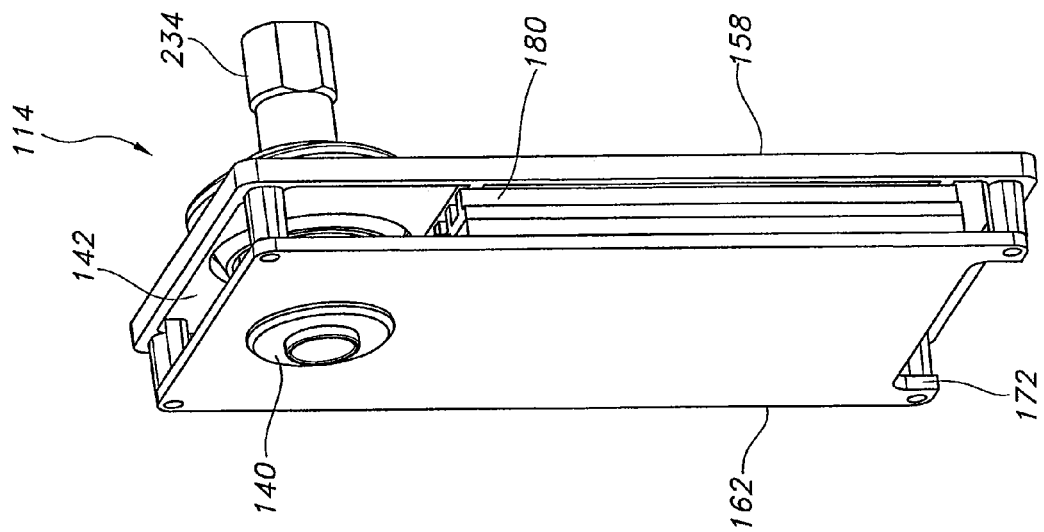
FIG. 8 is a perspective view of the gas heater illustrated in FIG. 7, with an insulator board portion of the gas heater removed.

Back-up plate 162 also includes a generally elongated opening 172 in the bottom thereof to provide fluid communication between first compartment 136 and second compartment 142. Additionally, back-up plate 162 further includes raised ridges 174 in a plurality of locations on second compartment side of flow divider 114. As shown in FIG. 6, four (4) raised ridges 174 are shown, although those skilled in the art will recognize that more or less than four raised ridges 174 may be used. Raised ridges 174 are used to locate an insulator board 176 on back-up plate 162 between upper and lower raised ridges 174.

An insulating gas heater 180 is disposed within second compartment 142 and is adapted to heat the second flow of gas. Insulating gas heater 180 is attached to insulator board 176 in second compartment 142. An exemplary insulating gas heater 180 is a heating plate having a plurality of elongated ribs 182 extending therefrom to dissipate heat generated from insulating gas heater 180 to surrounding gas flowing through second compartment 142. Insulating gas heater 180 may be constructed from aluminum or other suitable heat conductive material. Insulating gas heater 180 is electrically coupled to PC board 134 (shown in FIG. 9) such that PC board 134 controls operation of insulating gas heater 180.

Referring to FIG. 3A, in use, blower 112 directs air into flow divider 114, where the air is divided into first gas flow path 138 in first compartment 136 and second gas flow path 144 in second compartment 142. Gas within second gas flow path 144 is heated by insulating gas heater 180. Second gas flow path 144, having been heated by insulating gas heater 180, surrounds gas within first gas flow path 144 as the first gas flow passes from first compartment 136, through second compartment 142 and discharge port 140, and out of flow divider 114 to humidification canister 104.

Referring back to FIG. 5 a canister latch 194 releasably couples humidification canister 104 to base unit 102. Canister latch 194 is generally arcuate in shape and includes connectors 196 at each end for coupling to case top 120. In an alternative embodiment, latch 194 may be omitted, and humidification canister 104 may be releasably coupled to base unit 102 via a frictional engagement.

Referring back to FIG. 2, fluid heater 198 is configured to provide heat to humidification canister 104 (e.g., via conduction), which heats the fluid for heating and humidifying the first flow of gas in humidification canister 104. Fluid heater 198 is located on case top 120. Fluid heater 198 may be a conventional plate heater (which mates with a corresponding plate of humidification canister 104). Fluid heater 198 is electrically coupled to PC board 134 (shown in FIG. 9) such that PC board 134 controls operation of fluid heater 198.

Figure 9:
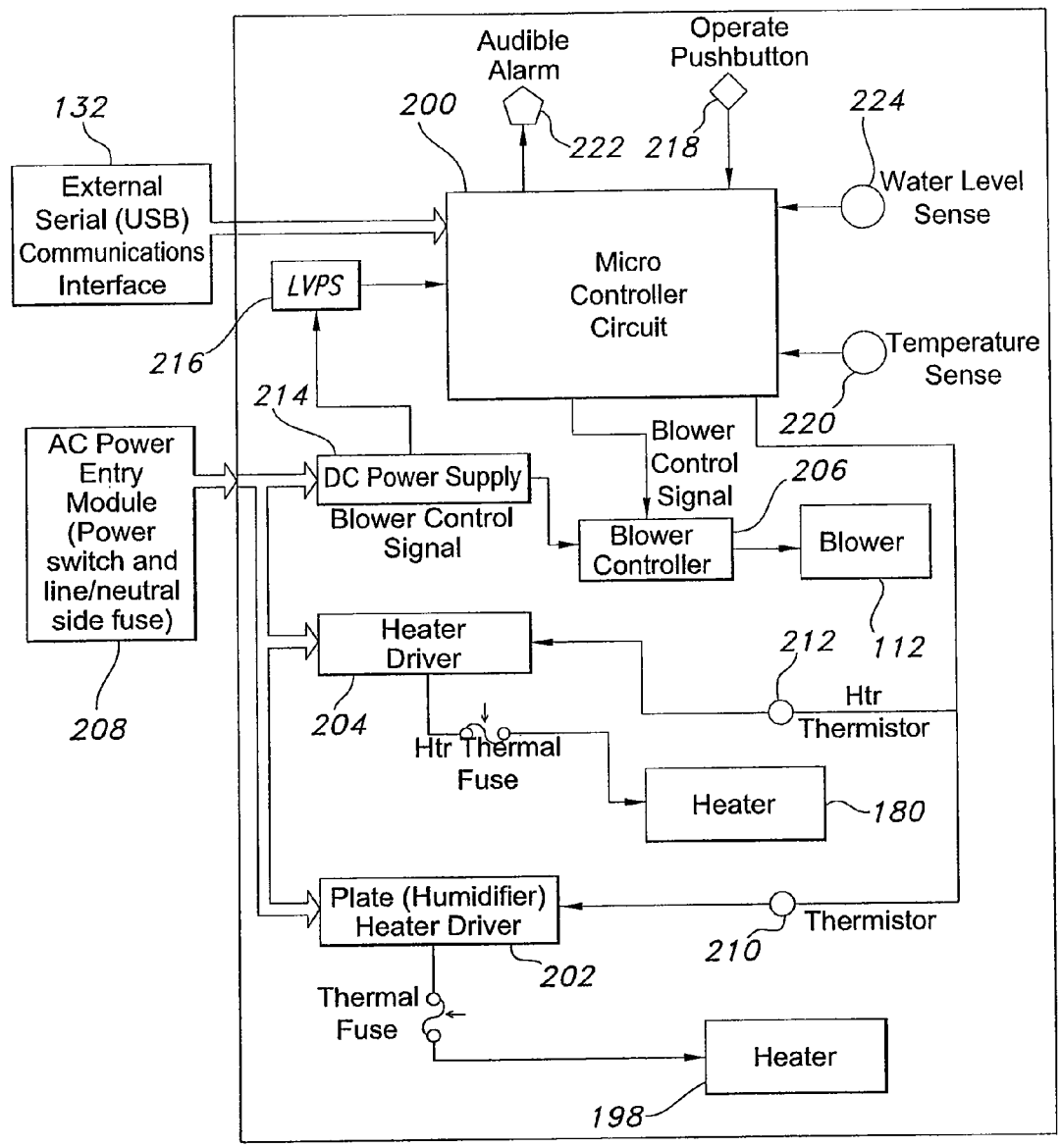
FIG. 9 is a schematic drawing of an exemplary control system used to operate the apparatus illustrated in FIG. 1.
Figure 10:
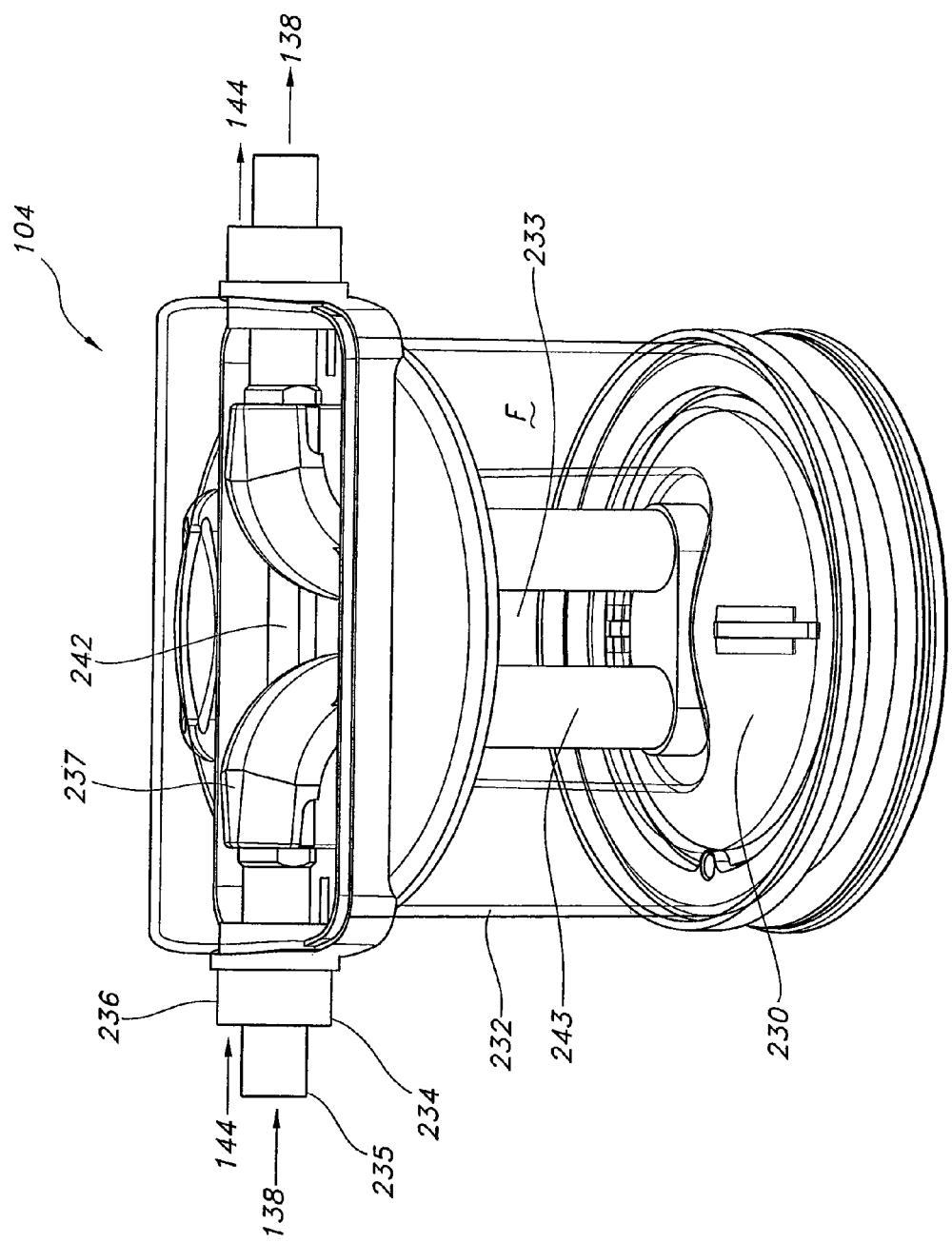
FIG. 10 is a perspective view of a humidification canister used in the apparatus illustrated in FIG. 1.

FIG. 9 depicts an exemplary control circuit 200 for controlling system 100 (FIGS. 1 and 2). Illustrated control circuit 200 is formed on PC board 134, which is removably inserted in slot 135 in case bottom 118 (shown in FIG. 4). Control circuit 200 provides control for three primary controllers. A first controller 202 is operatively coupled to humidifier heater 198 and, under control of control circuit 200, controls the temperature of humidifier heater 198 and regulates the temperature of the first flow of gas based on a delivery flow rate of the first flow of gas. A second controller 204, under control of control circuit 200, controls temperature of insulating gas heater 180, and a third controller 206, under control of control circuit 200, is configured to operate blower 112 to deliver the first flow of gas at a delivery flow rate. Control circuit 200 is accessible by an external computer (not shown) via a communications port, such as interface 132.

Interface 132 provides for adjustment of controllers 202, 204, 206, under control of control circuit 200, through the full range of operation of humidifier heater 198, insulating gas heater 180, and blower 112, respectively. An exemplary use of interface 132 is with system 100 in a sleep lab, where multiple users may be "titrated" using system 100 during a sleep study to determine ideal system settings for a particular user. Interface 132 may allow operational information for a particular user to be downloaded from an outside device, such as a USB device (not shown), to control circuit 200.

Electrically, this embodiment of system 100 operates within the range of 100-240 VAC and 50-60 Hz. The maximum power consumption is desirably less than about 60 Watts. Power inlet 208 includes a removable 3-meter long hospital grade power cord.

Control circuit 200 uses thermistors to sense temperature at various locations within system 100. Exemplary thermistors are rated at 15 KΩ@+25 C. A humidifier thermistor 210 measures the temperature of humidifier heater 198 to an accuracy of about +/−0.5° C. An air heater thermistor 212 measures the temperature of insulating gas heater 180 to an accuracy of about +/−0.5° C.

An AC power supply 208 provides AC power to system 100, including controllers 202, 204. In an exemplary embodiment, a 24 VDC power supply 214 capable of about 1 amp is used to power third controller 206. Alternatively, other power supplies, such as, for example, 12V at 2 amps, may be used.

Control circuit 200 provides speed control of blower 112 over an adjustable range of 0 to 100%, with a precision of about 1%+/−0.5%. Power supply 214 is also coupled to a Low Voltage Power Supply (LVPS) 216 that reduces the voltage to control circuit 200.

In an exemplary embodiment, control circuit gradually increases speed (ramp-up) to set blower speed over a predetermined period of time, such as, for example, twenty minutes. In an exemplary embodiment, every five minutes during ramp-up, blower speed will increase 25% until blower 112 reaches its set speed. Control circuit 200 includes a power button 218 that operates system 100. Power button 218 may be pressed a first time to power up system 100. If power button 218 is pressed a second time, the ramp function may be de-activated and blower 112 immediately goes to the speed set on control circuit 200.

After use, power button 218 may be pressed to turn off system 100. When system 100 is turned off, humidifier heater 198 turns off, but blower 112 and insulating gas heater 180 continue to run for a predetermined period of time, such as, for example, 1 minute, before turning off. Control circuit 200 may be configured to deactivate humidifier heater 198 if humidification canister 104 is not installed An optional ambient temperature sensor 220 monitors the ambient temperature around system 100 and feeds the recorded temperature to control circuit 200. Control circuit 200 may regulate insulating gas temperature by adjusting insulating gas heater 180 based on ambient temperature to maintain an approximate outlet temperature, such as about 37 degrees Celsius. Optionally, water level sensor 224 monitors the level of humidification fluid "F" in fluid supply reservoir 232 and feeds the recorded level to control circuit 200.

Control circuit 200 is configured to shutdown system 100 if predetermined parameters fall outside of a specified range. In an exemplary embodiment, such parameters may include, but are not necessarily limited to, breathing gas temperature (greater than 1 degree C. above set point), blower malfunction, insulating gas heater 180 (greater than 5 degrees C. above set point, and humidifier heater 198 (greater than 5 degrees C. above set point).

In an exemplary embodiment, insulating gas heater 180 and fluid heater 198 are regulated by control circuit 200 based on a set flow rate of blower 112, a comfort setting (described below), and, optionally, an ambient temperature value recorded by temperature sensor 220. In embodiments where ambient temperature is not employed, a look-up table may be used by control circuit 200 to select appropriate values for driving heater driver 204 for insulating gas heater 180 and heater driver 202 for fluid heater 198 based on the set rate of blower 112 and the comfort setting. In embodiments where ambient temperature is employed, separate look-up tables may be provided for different ambient temperature ranges. In accordance with this embodiment, a particular look-up table may be selected based on an ambient temperature value and, then, that look-up table may be used by control circuit 200 to select appropriate values for driving heater driver 204 for insulating gas heater 180 and heater driver 202 for fluid heater 198 based on the set rate of blower 112 and the comfort setting.

The use of an insulating gas heater 180 and a fluid heater 198 enables the temperature and the fluid content of the breathing gas to be independently regulated, thereby controlling relative humidity. For example, the setting of the fluid heater 198 may be used to regulate the amount of fluid in the breathing gas and the setting of the insulating gas heater 180 may be used to regulate the temperature of the breathing gas being delivered to the user. Relative humidity can be adjusted by increasing/decreasing the fluid content while holding the temperature of the breathing gas constant, maintaining the fluid content while increasing/decreasing the temperature, or increasing/decreasing the fluid content while increasing/decreasing the temperature. Suitable control logic and look-up tables to perform these tasks will be readily understood by one skilled in the art from the description herein.

In an exemplary embodiment, a physician, respiratory therapist, or other medical professional sets the flow rate of blower 112 prior to use of system 100. The user may then select from a plurality of comfort settings such as, for example, a "cool" setting (e.g., a breathing gas temperature to be delivered to user between about 30 and about 33 degrees Celsius with a relative humidity of between about 80% and about 100%), a "medium" setting (e.g., a breathing gas temperature to be delivered to user between about 33 and about 35 degrees Celsius with a relative humidity of between about 80% and about 100%), or a "warm" setting (e.g., a breathing gas temperature to be delivered to user between about 35 and about 37 degrees Celsius with a relative humidity of between about 80% and about 100%). Pushbutton 218 may include separate up and down buttons (not shown) that may be pressed to select a desired setting from among the plurality of available comfort settings.

Referring now to FIGS. 2 and 10-15A, humidification canister 104 is configured to heat and humidify the first flow, or portion, of the gas generated by blower 112 (not shown in FIGS. 10-15A). Humidification canister 104 includes a humidification chamber 230 that heats and humidifies the first flow, or breathing, gas, a fluid supply reservoir 232 that provides fluid "F", typically in the form of water, to humidify the breathing gas. Fluid supply reservoir 232 is operatively coupled to humidification chamber 230 to transmit water to humidification chamber 230 where the water is vaporized. Humidification canister 104 further includes an insulation chamber 233 that uses the second flow of the gas (insulating gas) to at least partially surround and insulate the breathing gas flowing through the first gas flow path of humidification canister 104, including humidification chamber 230. Second gas flow path 144 extends through insulation chamber 233 and provides fluid communication between blower 112 and delivery tube assembly 106.

Humidification canister 104 is operatively coupled to blower 112 to receive the first flow of gas along first gas flow path 138 and to receive the second flow of gas along second gas flow path 144. An inlet connector 234 includes a breathing gas lumen 235 that is in fluid communication with first compartment 136 (shown in FIG. 6) and extends from inlet grommet 161 in front cover 158, through second compartment 142, through back-up plate grommet 170 in back-up plate 162 to first compartment discharge port 140 such that first gas flow path 138 passes from first compartment 136 and into and through second compartment 142. An insulating gas lumen 236 extends through inlet grommet 161 in front cover 158 and is coaxially disposed around breathing gas lumen 235 downstream of flow divider 114 such that first gas flow path 138 and second gas flow path 144 are generally coaxial.

In an exemplary embodiment, breathing gas lumen 235 is also in fluid communication with a humidifier inlet elbow 237 that directs the breathing gas to a humidification chamber 230. Humidifier inlet elbow 237 is constructed from an outer elbow portion 238 and an inner elbow portion 239. Outer elbow portion 238 is part of a lid top 240 of humidification chamber 230 and inner elbow portion 239 is part of a lid bottom 241 of humidification chamber 230. A volume between lid top 240 and lid bottom 241 defines an insulating space 242 in fluid communication with insulating gas lumen 236 and insulating chamber 233.

Humidifier elbow 237 is coupled to an inlet baffle tube 243, which extends through an opening 232a in fluid supply reservoir 232 (shown in FIG. 14A). Inlet baffle tube 243 discharges into a humidification dome 244. Humidification dome 244 is generally conical in shape. Humidification dome 244 is removably coupled to bottom of fluid supply reservoir 232 such that humidification dome 244 may be removed from fluid supply reservoir 232 for replacement and/or cleaning.

Figure 12:
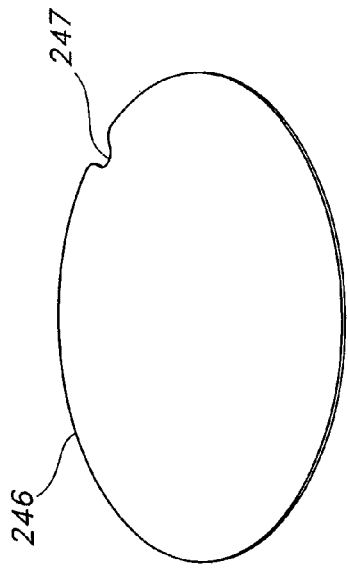
FIG. 12 is a perspective view of a filter media used in the humidification canister illustrated in FIGS. 10 and 11.
Figure 12A:
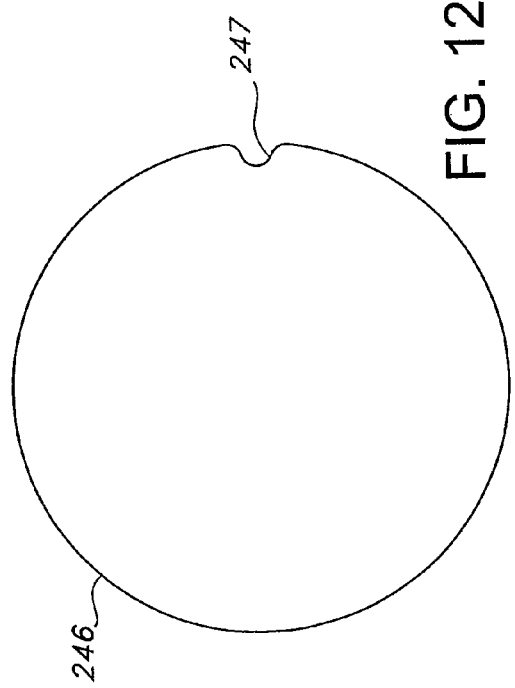
FIG. 12A is a top plan view of the filter media illustrated in FIG. 12.

A discharge end of inlet baffle tube 243 includes a baffle 245 that redirects breathing gas from a generally vertical downward direction to a generally horizontal direction. Referring to FIGS. 12 and 12A, a flat sheet membrane in the form of filter media 246 is disposed below humidification dome 244 and, together with humidification dome 244, filter media 246 defines humidification chamber 230. Filter media 246 is a generally circular piece of polytetrafluoroethylene (PTFE), which has an arcuate cutout 247 along its perimeter. The redirection of the breathing gas by baffle 245 may prevent the breathing gas from impinging directly onto the top surface of filter media 246, which may reduce wear of filter media 246. Additionally, the redirection of the breathing gas may improve the residence time of the breathing gas within humidification chamber 230, improving the heating and humidification of the breathing gas.

Figure 11:
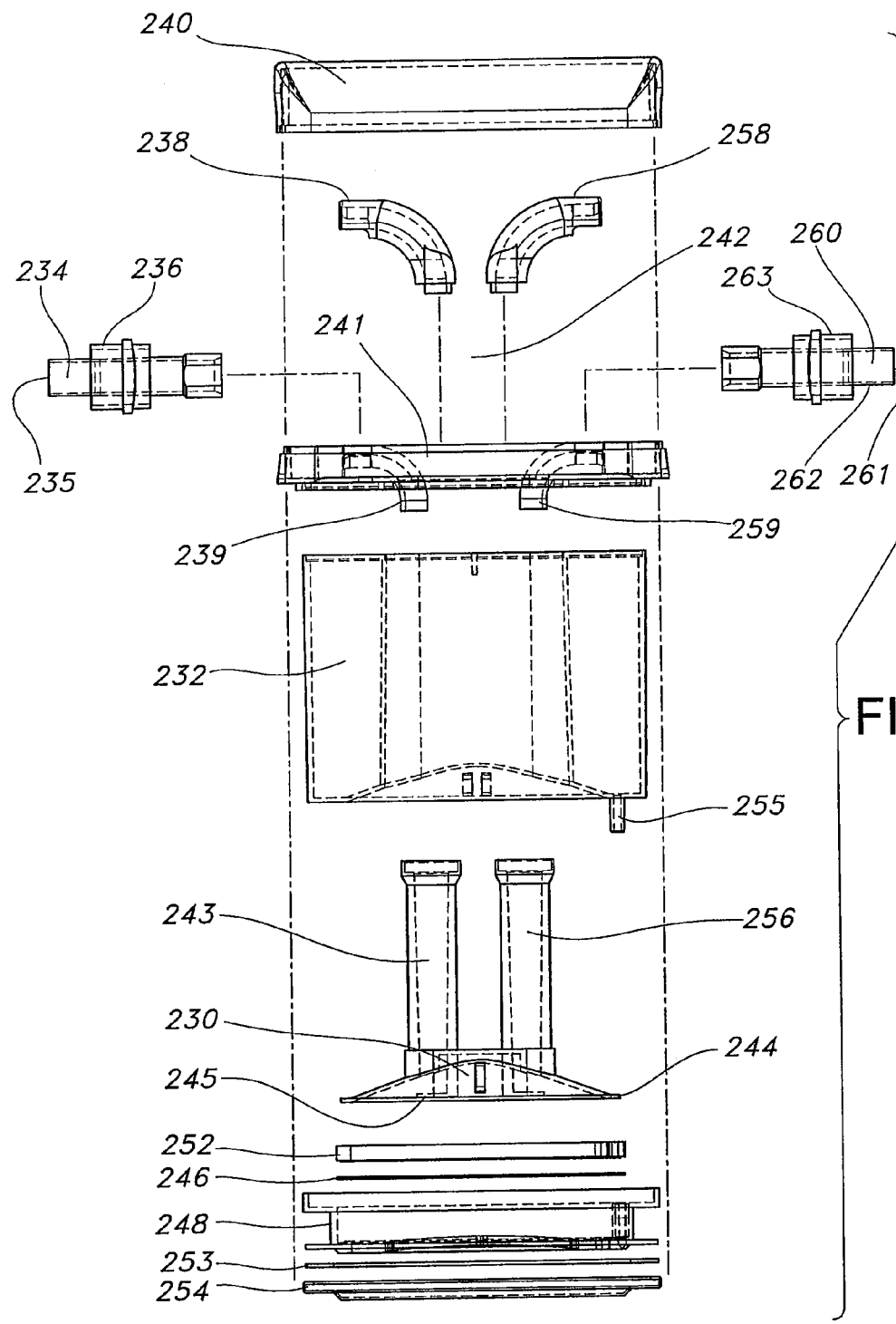
FIG. 11 is an exploded side view of the humidification canister illustrated in FIG. 10.

As shown in FIG. 11, filter media 246 is disposed in the path of fluid "F" between fluid supply reservoir 232 and humidification chamber 230, which is in first gas flow path 138. While fluid supply reservoir 232 is configured to hold fluid "F" in fluid communication with first gas flow path 138, filter media 246 restricts passage of fluid "F" from fluid supply reservoir 232 into first gas flow path 138 to introduce the proper amount of fluid "F" to humidification chamber 230.

Figure 13A:
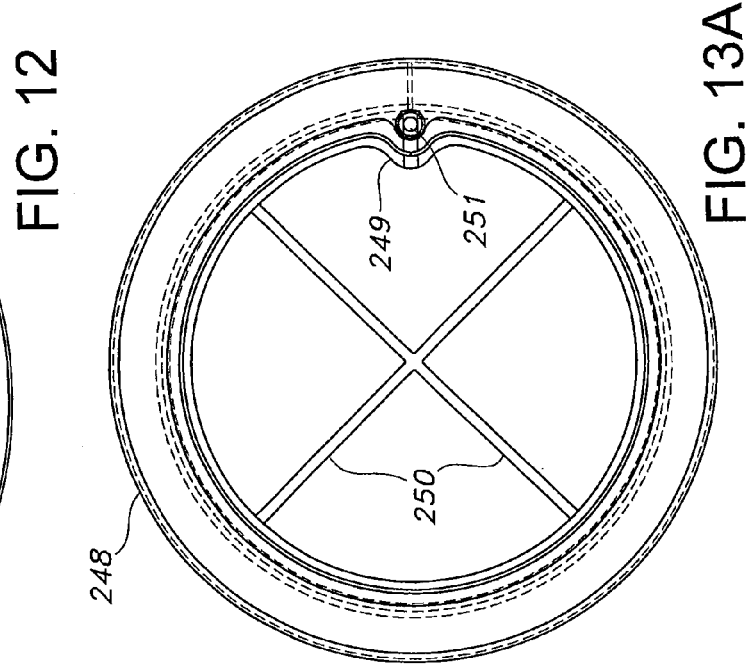
FIG. 13A is a top plan view of the media holder illustrated in FIG. 13.
Figure 13:
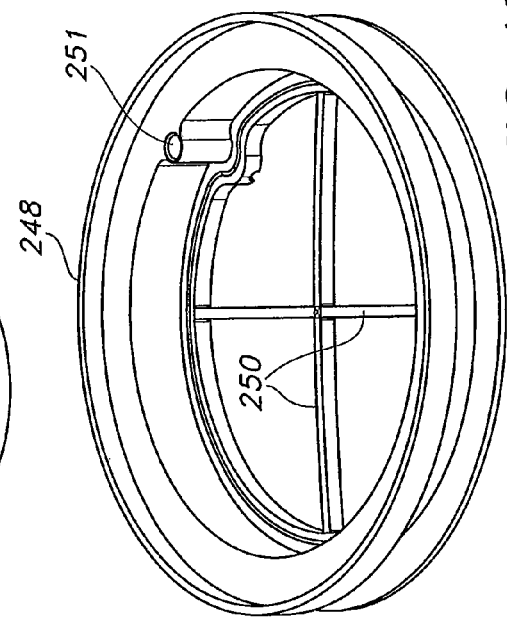
FIG. 13 is a perspective view of a media holder used in the humidification canister illustrated in FIGS. 10 and 11.

Filter media 246 is disposed within a media holder 248, which is shown in detail in FIGS. 13 and 13A. Media holder 248 includes an arcuate protrusion 249 sized to match arcuate cutout 247 in media filter 246. Media holder 248 includes a plurality of struts 250 that support filter media 246. Media holder 248 also includes an opening 251 proximate to arcuate protrusion 249.

Referring back to FIG. 11, a retaining ring 252 may be disposed over filter media 246 to retain filter media 246 on media holder 248. Although not shown, in an alternative embodiment, filter media 246 may be insert molded into a media holder, eliminating the need for retaining ring 252.

An annular tin gasket 253 is disposed under media holder 248. A circular tin heater plate 254 is disposed below gasket 253. When humidification canister 104 is coupled to base unit 102, heater plate 254 is disposed on top of fluid heater 198 to facilitate transfer of heat from fluid heater 198 to heater plate 254, which heats fluid that flowed from fluid supply reservoir 232 onto heater plate 254.

Referring now to FIGS. 2, 11, 14, and 14A, fluid supply reservoir 232 includes a drainage nipple 255 that extends from the bottom of fluid supply reservoir 232 and through opening 251 in media holder 248 to provide fluid communication from the interior of fluid supply reservoir 232 to the upper surface of heater plate 254. Optionally, although not shown, a valve, such as a Schrader valve, may be used to prevent fluid from flowing through drainage nipple 255 when fluid supply reservoir 232 is not coupled to base unit 102, but to open the valve when fluid supply reservoir 232 is coupled to base unit 102, to allow fluid flow from fluid supply reservoir 232 to heater plate 254. This valve prevents loss of fluid from fluid supply reservoir 232 when fluid supply reservoir 232 is not coupled to base unit 102, but allows for fluid communication between fluid supply reservoir 232 and humidification chamber 230 when fluid supply reservoir 232 is coupled to base unit 102.

Referring to FIGS. 2 and 11, an outlet baffle tube 256 is coupled to humidification dome 244 and extends from humidification chamber 230, through an opening 232b in fluid supply reservoir 232 (shown in FIG. 14A), to an outlet elbow 257. Outlet elbow 257 is constructed from an outer elbow portion 258 and an inner elbow portion 259. Outer elbow portion 258 is part of lid top 240 of humidification chamber 230 and inner elbow portion 259 is part of lid bottom 241 of humidification chamber 230.

Outlet elbow 257 is coupled to an outlet connector 260 which includes a breathing gas lumen 261 that is in fluid communication with outlet baffle tube 256 and an insulating gas lumen 262, coaxially disposed around breathing gas lumen 261, that is in fluid communication with insulation chamber 233 and insulating space 242. An exterior of illustrated outlet connector 260 includes a pair of diametrically opposed locking nubs 263 extending outwardly therefrom.

Referring to FIGS. 15 and 15A, lid bottom 241 includes an opening 264 therethrough. Opening 264 allows insulating space 242 to be in fluid communication with fluid "F" in fluid supply reservoir 232, providing a pressurization path between second gas flow path 144 and fluid supply reservoir 232 to pressurize fluid supply reservoir 232 with the second flow of gas.

Lid bottom 241 also includes a refill opening 265 that is in fluid communication with fluid supply reservoir 232 such that a cover (not shown) can be removed from refill opening 265 so that fluid can be added through refill opening 265 to replenish fluid "F" in fluid supply reservoir 232.

First gas flow path 138 extends through humidification canister 104 from breathing gas lumen 235, through humidifier inlet elbow 237, down inlet baffle tube 243, to humidification chamber 230 where breathing gas in first gas flow path 138 is heated and humidified. The heated and humidified breathing gas exits humidification chamber 230 through outlet baffle tube 256, through outlet elbow 257 to breathing gas lumen 261 for discharge from humidification canister 104.

Figure 16:
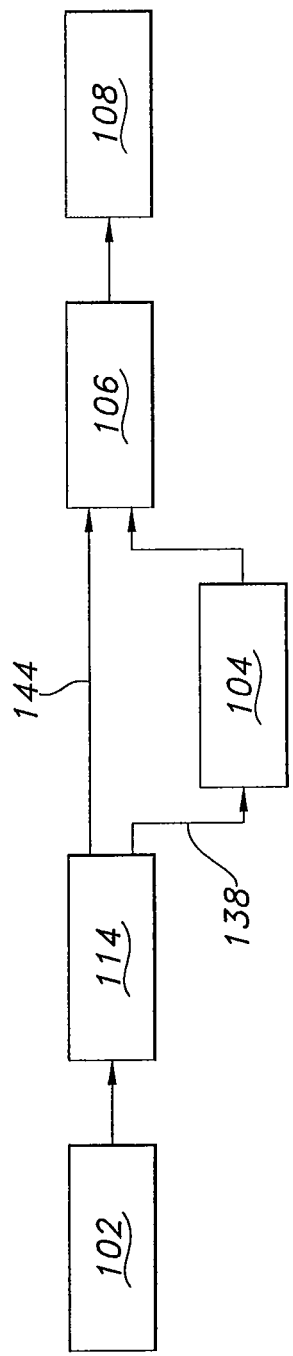
FIG. 16 is a schematic view of an apparatus for providing breathing gas to a user according to an alternative exemplary embodiment of the present invention.

In an alternative embodiment, as shown in the schematic drawing of FIG. 16, second gas flow path 144 may bypass humidification canister 104 such that second gas flow path 144 extends directly from flow divider 114 to delivery tube assembly 106.

While exemplary embodiments of a humidification canister 104 are shown, those skilled in the art will recognize that other embodiments of humidification canisters from the description herein are contemplated by the present invention and such embodiments are considered within the scope of the present invention.

Although air/gas is used to insulate the breathing gas in the exemplary embodiment, it is contemplated that water/liquid may be used for insulating/heating breathing gas in addition to or instead of air/gas.

Delivery tube assembly 106 is used to deliver the breathing gas from humidification canister 104 to the user. Referring now to FIGS. 2 and 17-26, illustrated delivery tube assembly 106 includes a multilumen delivery tube having a first, or inner, lumen 270 and a second, or outer lumen 276. Lumen 270 has an upstream portion 272 in fluid communication with humidification chamber 230 and with first gas flow path 138 to receive humidified breathing gas from humidification canister 104 and a downstream portion 274 configured to deliver the humidified breathing gas to nasal cannula 108 or other breathing device. First lumen 270 is configured to deliver the breathing gas from upstream portion 272 to downstream portion 274.

Outer lumen 276 is adjacent to and at least partially surrounds inner lumen 270 such that inner lumen 270 is disposed within outer lumen 276. Outer lumen 276 is in fluid communication with insulation chamber 233 and with second gas flow path 144 to receive the second flow of gas. Outer lumen 276 is configured to pass the second flow, or insulating, gas around inner lumen 270. Outer lumen 276 is configured for coupling to humidification canister 104 to receive the insulating gas and is adapted to transmit the insulating gas from humidification canister 104 along the length of inner lumen 270 and to discharge the insulating gas to atmosphere.

In an exemplary embodiment, inner lumen 270 may be a tube, such as Model No. Type 777, manufactured by Hi-Tech Medical of Georgetown, Mass., having an inner diameter of about 10 mm. Inner lumen 270 may have a length of about 180 cm. Upstream portion 272 and downstream portion 274 of inner lumen 270, as well as an inner surface of inner lumen 270, may be generally smooth. An outer surface 278 of inner lumen 270 between upstream end 272 and downstream end 274 may be corrugated. Such corrugation reduces the likelihood of kinking inner lumen 270 and also provides for coupling of spacers to the exterior of inner lumen 270.

In an exemplary embodiment, outer lumen 276 may be a tube, such as Model No. Type 555, manufactured by Hi-Tech Medical of Georgetown, Mass. having an inner diameter of about 19 mm. Outer lumen 276 may have a length of about 180 cm. Outer lumen 276 may have a generally smooth upstream end 280 and inner surface, and a corrugated outer surface 282 that extends downstream of upstream end 280. Such corrugation reduces the likelihood of kinking cannula 108.

Referring to FIGS. 18-20, a plurality of spacers 284 are disposed within outer lumen 276 such that inner lumen 270 is generally centered within outer lumen 276. Spacers 284 may be spaced about 30 cm apart along the corrugated portion of inner lumen 270. Each spacer 284 includes an arcuate frame 286 extending in a plane and a plurality of longitudinal struts 288 extending generally perpendicular to the plane. Arcuate frame 286 is sized to fit in a groove between adjacent ridges of the exterior of corrugated inner lumen 270. Arcuate frame 286 extends in an arc of over 180 degrees such that arcuate frame 286 can be snapped over groove. In an exemplary embodiment, arcuate frame 286 extends in an arc of about 240 degrees. Longitudinal struts 288 engage interior wall of outer lumen 276.

Figure 23:
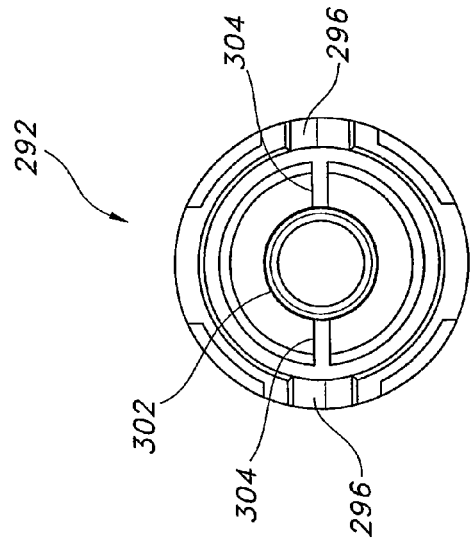
FIG. 23 is an end view of the twist lock connection illustrated in FIG. 21.
Figure 21:
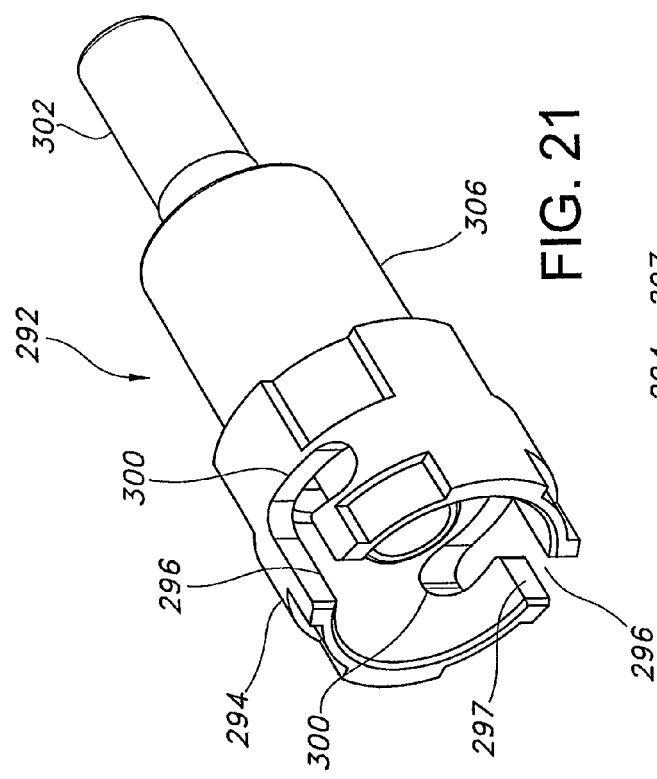
FIG. 21 is a perspective view of a twist lock connection used in the delivery tube assembly illustrated in FIGS. 17 and 18.
Figure 22:
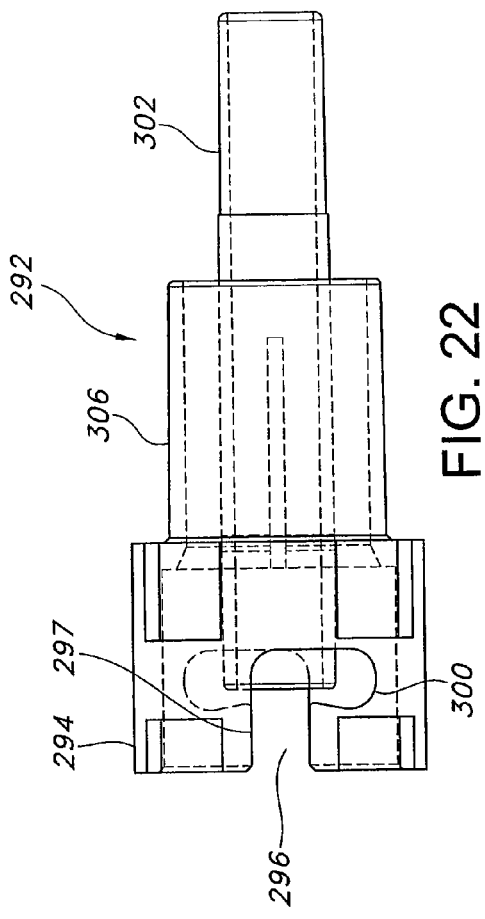
FIG. 22 is a side view of the twist lock connection illustrated in FIG. 21.

Referring back to FIG. 17-18 and to FIGS. 21-23, an upstream portion 290 of delivery tube assembly 106 includes a twist lock connector 292 that is adapted to releasably couple delivery tube assembly 106 to humidification canister 104. In an exemplary embodiment, twist lock connector 292 may be constructed from high density polyethylene (HDPE), polypropylene, or other suitable material. Twist lock connector 292 includes a base portion 294 having a pair of diametrically opposed slots 296, with a first slot portion 297 extending toward downstream portion 298 (shown in FIG. 17) of delivery tube assembly 106. A second slot portion 300 of each of slots 296 extends transversely to first slot portion 297. Locking nubs 263 from humidification canister 104 (shown in FIG. 11) are sized to fit into first slot portion 297 as twist lock connector 292 is advanced over outlet connector 260. When twist lock connector 292 is advanced such that locking nubs 263 are at the intersection between first slot portion 297 and second slot portion 300, twist lock connector 292 is rotated such that locking nubs are advanced to the closed end of second slot portion 300, thereby releasably coupling delivery tube assembly 106 to humidification canister 104.

Twist lock connector 292 further includes an inner lumen portion 302 that extends downstream from base portion 294. Inner lumen portion 302 is coupled to base portion 294 via a pair of diametrically opposed spacers 304. Twist lock inner lumen portion 302 is coupled to upstream end 272 of inner lumen 270.

Twist lock connector 292 also includes an outer lumen portion 306 that extends downstream from base portion 294. Outer lumen portion 306 is coupled to an outer perimeter of base portion 294. Twist lock outer lumen portion 306 is coupled to upstream end 280 of outer lumen 276.

Referring to FIGS. 17, 18, and 24-26, delivery tube assembly 106 further includes a flow diverter assembly 310 coupled to downstream portion 274 of inner lumen 270. Diverter assembly 310 is adapted to divert the insulating gas flowing through outer lumen 276 in a direction away from downstream portion 274 of inner lumen 270 to atmosphere. Diverter assembly 310 is swivelly coupled to downstream portion 274 of the inner lumen 270 to reduce potential kinking of cannula 108 during use.

FIGS. 24-26 illustrate an exemplary flow diverter assembly 310. Flow diverter assembly 310 includes an input portion 312, a discharge portion 314, and a diverter portion 316 disposed between input portion 312 and discharge portion 314. Fins 318 space diverter portion 316 from outer lumen 276. Breathing gas, shown in FIGS. 24 and 26 as arrow A, flows from inner lumen 270 (shown in FIG. 26), through input portion 312 and discharge portion 314 to nasal cannula 180 (not shown in FIG. 24). Insulating gas, shown in FIG. 24 as arrow B, flows from outer lumen 276, through input portion 312 to diverter portion 316, where the insulating gas is diverted (e.g. about 180 degrees) and discharged from diverter assembly 310 and away from the user.

Using air/gas instead of water to insulate the breathing gases and exhausting the insulating gas to atmosphere eliminates the need for a heating fluid recirculation system, reduces the potential for leaks and bacterial contamination, and enables a lightweight delivery tube to be used in the system.

Figure 27:
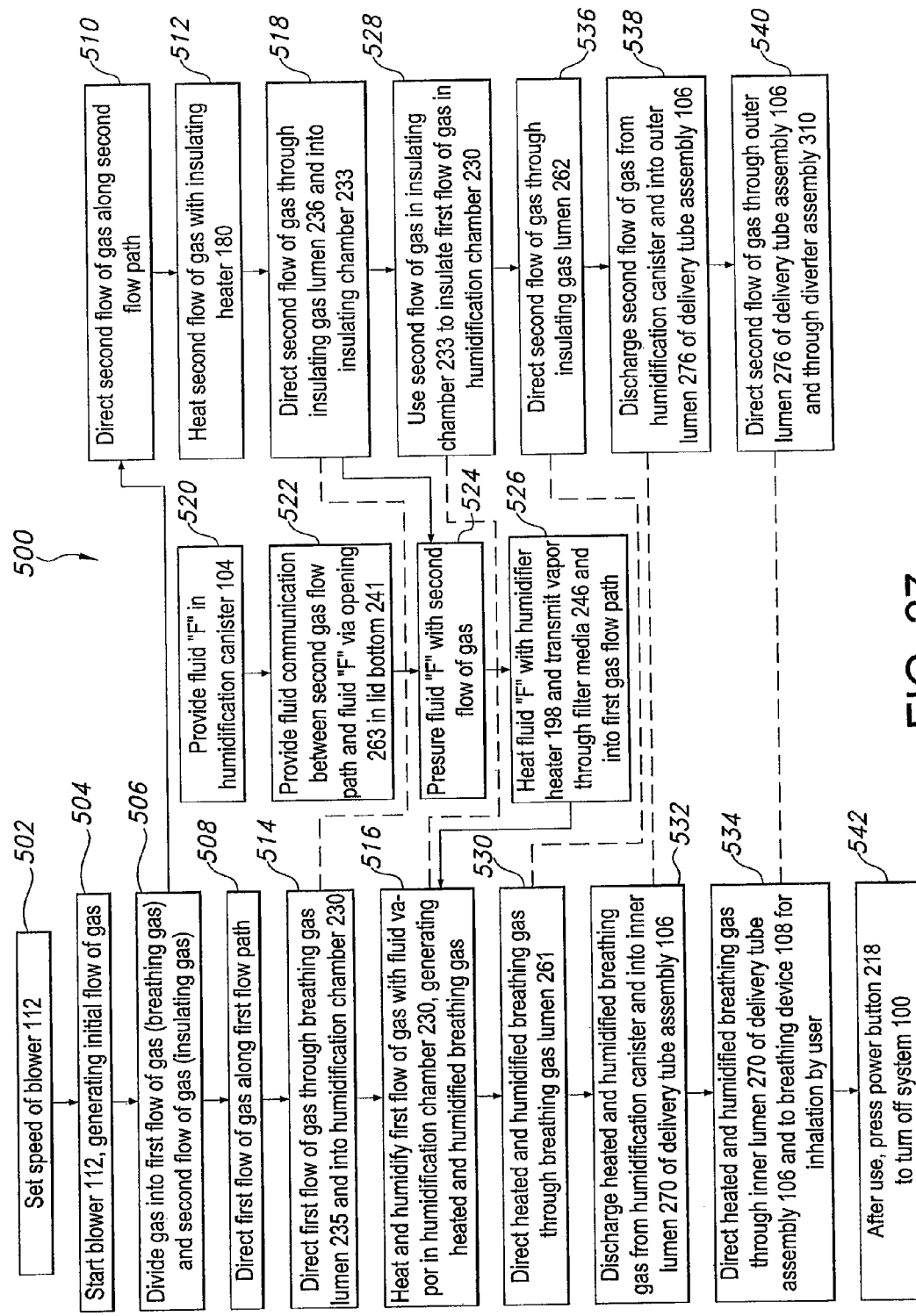
FIG. 27 is a flow chart illustrating exemplary operational steps of the apparatus illustrated in FIGS. 1-26.

Referring to FIGS. 1-26 and the flow chart 500 of FIG. 27, an exemplary operation of system 100 is as follows. In STEP 502 the speed of blower 112 is set. In an exemplary embodiment, a professional, such as a physician or a respiratory therapist, determines a desired flow rate of breathing gas to be administered to the user, and adjusts control circuit 200 to control third controller 206 to set a speed of blower 112. By setting third controller 206 to the desired setting, a rate of an initial flow of gas, which is the total of a rate of the first flow of gas (the breathing gas) and a rate of the second flow of gas (the insulating gas), is set. In an alternative exemplary embodiment, a person receiving the therapy may set the flow rate.

In STEP 504, blower 112 is started. In an exemplary embodiment, the user presses power button 218, resulting in control circuit 200 starting blower 112, as well as transmitting signals to first controller 202 and second controller 204 to operate insulating gas heater 180 and humidifier heater 198. The starting of blower 112 generates an initial flow of gas. In STEP 506 the initial flow of gas is divided into a first flow of gas and a second flow of gas. In an exemplary embodiment, the initial flow of gas flows into flow divider 114, where the initial flow of gas is divided into the first flow of gas in first compartment 136 for breathing and the second flow of gas in second compartment 142 for insulating the first flow of gas. In STEP 508, the first flow of gas flows along first gas flow path 138, while in STEP 510, the second flow of gas flows along second gas flow path 144. As shown in the flow chart 500, the breathing gas and the insulating gas flow in generally parallel paths.

In STEP 512, the second flow of gas is heated. In an exemplary embodiment, the second flow of gas is heated by insulating gas heater 180 as the second flow of gas flows through second compartment 142. In an exemplary embodiment, the second flow of gas is heated for use in insulating at least a portion of the first flow of gas in the first gas flow path 138.

In STEP 514, the breathing gas flow is directed along first gas flow path 138. In an exemplary embodiment, first gas flow path 138 includes humidification chamber 230. The flow of the breathing gas is directed through breathing gas lumen 235, which is the inlet to humidification chamber inlet 230.

In STEP 516, humidification fluid is heated. In an exemplary embodiment, as the breathing gas flows along first gas flow path 138 through humidification chamber 230, humidifier heater plate 254 heats fluid "F" that has flowed from fluid supply reservoir 232 to top of heater plate 254. The heated fluid passes through filter media 246 and into first gas flow path 138 within humidification chamber 230, where the heated fluid vaporizes. The vaporized fluid heats and humidifies the first flow of gas in first gas flow path 138. The flow of the now heated and humidified breathing gas is then directed through breathing gas lumen 261, which is the outlet of humidification chamber 230.

In STEP 518, the flow of the insulating gas is directed along second gas flow path 144. In an exemplary embodiment, second gas flow path 144 includes insulating chamber 233, which at least partially surrounds humidification chamber 230. The flow of the insulating gas is directed through insulating gas lumen 236, which is the inlet to insulating chamber 233. The flow of the insulating gas is directed through insulating gas lumen 262, which is the outlet from insulating chamber 233. Throughout STEP 518, the insulating gas provides insulation to and regulates the temperature of the breathing gas (e.g., by minimizing the temperature drop of the breathing gas).

Further, humidification fluid "F" within fluid supply reservoir 232 is pressurized by the insulating gas within humidification canister 104. In STEP 520, humidification fluid is provided. In an exemplary embodiment, the supply of the humidification fluid "F" is provided within humidification canister 104 to humidify the breathing gas. In STEP 522, fluid communication is also provided between second gas flow path 144 and supply of humidification fluid "F." In an exemplary embodiment, the fluid communication is provided via opening 263 in lid bottom 241 of humidification canister 104 such that, in STEP 524, humidification fluid "F" is pressurized with the insulating gas. In STEP 526, fluid "F" is heated. In an exemplary embodiment, fluid "F" is heated with humidifier heater 198, which is transmitted through filter media 246 and into first gas flow path 138. In STEP 516, the breathing gas is humidified. In an exemplary embodiment, the breathing gas is humidified in humidification chamber 230. In STEP 528, the insulating gas insulates the breathing gas. In an exemplary embodiment, the insulating gas in insulating chamber 233 insulates the breathing gas in humidification chamber 230.

In STEP 530 the heated and humidified breathing gas is discharged from humidification canister 104. In an exemplary embodiment, the heated and humidified breathing gas is directed through breathing gas lumen 261 in humidification canister 104 and then, in STEP 532, the heated and humidified breathing gas is discharged into delivery tube assembly 106. In STEP 534, the heated and humidified breathing gas flows through delivery tube assembly 106. In an exemplary embodiment, the heated and humidified breathing gas flows through first, or inner, lumen 270 in a first direction from upstream portion 272 to downstream portion 274 of inner lumen 270. The breathing gas is discharged from the downstream end of delivery tube assembly 106 into breathing device 108 for inhalation by the user.

In STEP 536, the insulating gas is discharged from humidification canister 104. In an exemplary embodiment, the insulating gas is directed through insulating gas lumen 262 and out of humidification canister 104. In STEP 538, the breathing gas is received in the upstream end of delivery tube assembly 106. In STEP 540, the insulating gas at least partially insulates the breathing gas. In an exemplary embodiment, the insulating gas flows through second, or outer, lumen 276, wherein the insulating gas at least partially insulates the heated and humidified breathing gas. The insulating gas also flows in the first direction from upstream to downstream. In an exemplary embodiment, the insulating gas is discharged to atmosphere from downstream end of delivery tube assembly 106 through diverter assembly 310, which diverts the insulating gas away from the user.

In STEP 542, after use, system 100 is turned off. In an exemplary embodiment, when the user presses power button 218 to turn off system 100, humidifier heater 198 turns off but blower 112 and insulating heater 180 continue to run for a predetermined period of time, such as, for example, 1 minute, before turning off. Additionally, control circuit 200 may be configured to deactivate humidifier heater 198 if humidification canister 104 is not installed Referring to FIG. 27 dashed lines connecting STEPS 514-518, 516-528, 530-536, 532-538, and 524-538 indicate locations along first gas flow path 138 where the breathing gas is or may be insulated by the insulating gas flowing along second gas flow path 144.

Ambient temperature sensor 220 monitors the ambient temperature around system 100 and feeds the recorded temperature to control circuit 200. Control circuit 200 regulates insulating gas temperature by adjusting the insulating heater 180 to maintain an approximate outlet temperature of the insulating gas, such as about 37 degrees Celsius.

While an exemplary embodiment of a breathing assistance system 100 and its operation are described above, the present invention may encompass other embodiments as well. As discussed above, gas flow source may comprise a plurality of sources. In the exemplary embodiment of a breathing gas delivery system 700 shown in FIG. 28, a first source of gas 702 may be a compressed gas, such as oxygen. A second source of gas 704 may be air, generated by a blower. Alternatively, both first source of gas 702 and second source of gas 704 may be blowers. Also, both gas sources 702, 704 may be compressed gas sources such as oxygen and/or air from a high pressure source.

Additionally, in an alternative embodiment of a breathing system 709 shown schematically in FIG. 29, an auxiliary gas port 710 may extend from an upstream end 712 of an inner lumen 714 to facilitate connection of a pressurized gas source, such as oxygen, for inhalation by a user through nasal cannula 108.

Further, an alternative embodiment of a delivery tube assembly 600, shown in cross section in FIG. 30, uses a plurality of fins 601 formed with or coupled to the exterior of inner lumen 602 to space inner lumen 602 generally coaxially within an outer lumen 604.

Still another alternative embodiment of a delivery tube assembly 800 may be used instead of delivery tube assembly 106. As shown in cross section in FIG. 31 and schematically in FIG. 32, first lumen 802 may be generally centrally disposed within delivery tube assembly 800, with a second lumen 804 comprising a first lumen portion 806 extending approximately the length of first lumen 802, and a second lumen portion 808 extending approximately the length of first lumen 802. First and second lumen portions 806, 808 surround first lumen 802. First and second lumen portions 806, 808 may be generally "C-shaped" in cross section. A septum 810 separates first lumen 802 from each of first and second lumen portions 806, 808. At a downstream end 814 of assembly 800, first lumen portion 806 and second lumen portion 808 are in fluid communication with each other and at an upstream end 814 of assembly 800, first lumen portion 806 and second lumen portion 808 are not in fluid communication with each other.

In operation, breathing gas enters first lumen 802 from humidification canister 104 and travels through the length of first lumen 802, where the breathing gas is discharged to nasal cannula 108. Insulating gas enters first lumen portion 806 from humidification canister 104 at upstream end 816 of assembly 800 and travels through first lumen portion 806 to downstream end 814 of assembly 800. The insulating gas then enters second lumen portion 808 and travels through second lumen portion 808 to upstream end 816 of assembly 800, where the insulating gas discharges to atmosphere.

Figure 31:
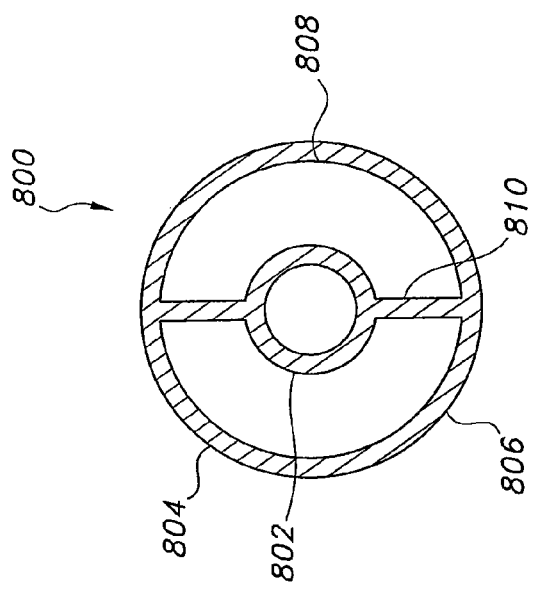
FIG. 31 is a sectional view of a delivery tube assembly according to yet another exemplary embodiment of the present invention.
Figure 32:
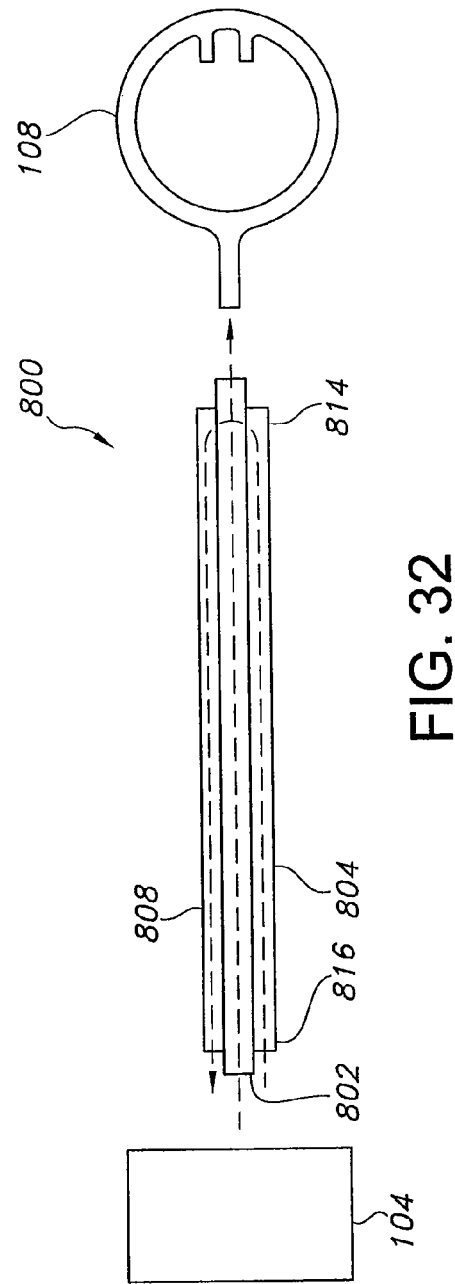
FIG. 32 is a schematic view of an apparatus for providing breathing gas to a user using the delivery tube assembly illustrated in FIG. 31 according to another exemplary embodiment of the present invention.

In yet another alternative embodiment of a delivery tube assembly 900, shown schematically in FIG. 33, delivery tube assembly 900 has a similar cross section to delivery tube assembly 800 shown in FIG. 31 and may include a first, inner lumen 902 that has an upstream end 904 configured to couple to humidification canister 104 and a downstream end 906 configured to couple to nasal cannula 108 such that the breathing gas flows through first lumen 902 from upstream end 904 to downstream end 906.

Delivery tube assembly 900 also includes a second lumen 908 having a first lumen portion 910 and a second lumen portion 912 which, together, generally surround first lumen 902. First lumen portion 910 and second lumen portion 912 may be generally "C-shaped" in cross section (similar to lumen portions 806, 808 shown in FIG. 31. Delivery tube assembly 900 includes a diverter assembly, such as diverter assembly 310 illustrated in FIGS. 17, 18, and 24-26 and described above, that is coupled to downstream end 906 first lumen 902. Diverter assembly 319 redirects the insulating gas flowing through first lumen portion 910 and a second lumen portion 912 away from the user and to atmosphere.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A delivery tube assembly for delivering a breathing gas to a patient, the delivery tube comprising: a first lumen having an upstream portion positionaly away from the patient and a downstream portion towards the patient, the lumen configured to deliver the breathing gas from the upstream portion to the downstream portion; a second lumen having an upstream portion and a downstream portion and at least partially surrounding the first lumen and configured to flow an insulating gas in the same direction as the breathing gas around the first lumen; and a diverter assembly coupled to the downstream portion of the first lumen and the second lumen, the diverter assembly adapted to pass a flow of the breathing gas therethrough and to divert the insulating gas into the atmosphere in a direction substantially opposite the flow of the breathing gas and positionaly away from the patient.

2. The delivery tube assembly according to claim 1, wherein the first lumen is disposed within the second lumen.

3. The delivery tube assembly according to claim 2, further comprising a plurality of spacers disposed within the second lumen such that the first lumen is generally centered within the second lumen.

4. The delivery tube assembly according to claim 3, wherein each of the plurality of spacers comprises an arcuate frame extending in a plane and a plurality of longitudinal struts extending generally perpendicular to the plane.

5. The delivery tube assembly according to claim 3, wherein each of the plurality of spacers comprises a fin coupled to the first lumen.

6. The delivery tube assembly according to claim 1, wherein the diverter assembly is swivelly coupled to the downstream portion of the first lumen.

7. The delivery tube assembly according to claim 1, wherein the second lumen comprises a first lumen portion extending between the upstream portion of the first lumen and the downstream portion of the first lumen, and a second lumen portion extending from the downstream portion of the first lumen portion and toward the upstream portion of the first lumen, wherein the first lumen portion is in fluid communication with the second lumen portion at the downstream portion of the first lumen.

8. A delivery tube assembly configured to be coupled to a humidifier, the delivery tube assembly comprising: an inner lumen with an upstream portion configured to receive humidified breathing gas from the humidifier and a downstream portion configured to deliver the humidified breathing gas to a patient; an outer lumen surrounding the inner lumen, the outer lumen is coupled to the humidifier and is configured to receive an insulating gas, wherein the insulating gas and the humidified breathing gas travel in the same direction; and a diverter assembly coupled to the inner lumen proximate to the downstream portion of the outer lumen, the diverter assembly adapted to pass a flow of the humidified breathing gas therethrough and to divert the insulating gas into the atmosphere in a direction substantially opposite the flow of the humidified breathing gas and positionaly away from the patient.

9. A delivery tube assembly for delivering a breathing gas to a patient comprising: an inner lumen adapted to transmit a breathing gas; an outer lumen at least partially surrounding the inner lumen, the outer lumen adapted to transmit an insulating gas in the same direction as the breathing gas and discharge the insulating gas to atmosphere; and a diverter assembly coupled to the inner and the outer lumen and configured to pass a flow of the breathing gas therethrough, the diverter assembly is positioned to divert the insulating gas being discharged from the outer lumen to the atmosphere, the diverter assembly having an outlet configured to discharge the insulating gas along substantially an entire circumference of the outer lumen and positionaly away from the patient.

10. The delivery tube assembly according to claim 9, wherein the outer lumen is adapted to transmit the insulating gas along the length of the inner lumen.

11. A method of insulating heated and humidified breathing gas with an insulating gas in a delivery tube assembly having a first lumen and a second lumen, the method comprising the steps of:
 a) flowing the heated and humidified breathing gas through the first lumen in a first direction;
 b) flowing the insulating gas through the second lumen surrounding the first lumen in the first direction, wherein the insulating gas at least partially insulates the heated and humidified breathing gas;
 c) passing the flow of the heated and humidified breathing gas through a diverter assembly; and
 d) diverting the flow of the insulating gas into the atmosphere in a second direction substantially opposite the first direction with the diverter assembly.

12. The method according to claim 11, further comprising the step of, prior to step b), heating the insulating gas.

13. A method of insulating a breathing gas with an insulating gas and discharging the insulating gas to atmosphere, the method comprising the steps of:
 a) receiving the breathing gas in a distal end of an inner lumen of a delivery tube;
 b) receiving the insulating gas in the distal end of an outer lumen of the delivery tube;
 c) discharging the breathing gas from a proximal end of the delivery tube into a breathing device;
 d) flowing the insulating gas from the distal end of the delivery tube, through the delivery tube, to the proximal end of the delivery tube;
 e) directing the breathing gas and the insulating gas from the distal end of the delivery tube to the proximal end of the delivery tube;
 e) discharging the insulating gas from the delivery tube to atmosphere with a diverter assembly coupled to the delivery tube, the diverter assembly having an outlet configured to discharge the insulating gas along substantially an entire circumference of the delivery tube and towards the distal end, wherein the diverter assembly is configured to pass the breathing gas therethrough.

14. The method according to claim 13, further comprising the step of, prior to step b), heating the insulating gas.

* * * * *